United States Patent
Adair

(10) Patent No.: US 8,119,134 B2
(45) Date of Patent: *Feb. 21, 2012

(54) METHOD FOR EXTENDING PREGNANCY IN PATIENTS EXHIBITING AT LEAST ONE SYMPTOM OF PREECLAMPSIA AND ECLAMPSIA

(75) Inventor: Charles David Adair, Signal Mountain, TN (US)

(73) Assignee: Glenveigh Pharmaceuticals, LLC, Chattanooga, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/849,651

(22) Filed: Aug. 3, 2010

(65) Prior Publication Data

US 2010/0297129 A1 Nov. 25, 2010

Related U.S. Application Data

(62) Division of application No. 11/317,378, filed on Dec. 23, 2005, now Pat. No. 7,794,716.

(60) Provisional application No. 60/681,693, filed on May 17, 2005.

(51) Int. Cl.
*A61K 39/395* (2006.01)
(52) U.S. Cl. ........... 424/133.1; 424/145.1; 424/158.1; 514/15.6; 530/387.3; 530/388.24
(58) Field of Classification Search .............. None
See application file for complete search history.

(56) References Cited

U.S. PATENT DOCUMENTS

| 6,290,657 B1 * | 9/2001 | Adams et al. ............ 600/591 |
| 7,402,313 B2 * | 7/2008 | Adair ..................... 424/133.1 |
| 7,794,716 B2 * | 9/2010 | Adair ..................... 424/133.1 |

OTHER PUBLICATIONS

Adair et al., Am. J. Nephrol., 1996, 16:529-531.*
Adair et al., Am. J. Hypertension, 1997, vol. 10, supplement 1, p. 11A.*
The Merck Manual of Diagnosis and Therapy, 17th ed., 1999, editors Beers and Berkow, pp. 2057-2058.*
Product Information Insert for DIGIBIND, GlaxoSmithKline, digoxin immune Fab (ovine) 2001, pp. 1-8.*

* cited by examiner

*Primary Examiner* — Michael Szperka
(74) *Attorney, Agent, or Firm* — Hunton & Williams LLP

(57) ABSTRACT

A composition is provided to prevent, limit the effects of, delay the onset of, or treat one or more of the causes, symptoms or complications of gestational hypertension, preeclampsia, eclampsia and/or intrauterine growth restriction. The composition comprises a therapeutically effective amount of an antibody that reacts immunologically with or binds digoxin and has a high dose of digoxin binding capacity as the active ingredient. There is also provided a method of preventing, limiting the effects of, delaying the onset of, or treating a cause, symptom or complication of gestational hypertension, preeclampsia, eclampsia or intrauterine growth restriction, comprising the step of administering to a mammal a composition comprising a therapeutically effective amount of an antibody that reacts immunologically with or binds digoxin and has a high dose of digoxin binding capacity.

28 Claims, 4 Drawing Sheets

METHOD FOR EXTENDING PREGNANCY IN PATIENTS EXHIBITING AT LEAST ONE SYMPTOM OF PREECLAMPSIA AND ECLAMPSIA

CROSS-REFERENCE TO RELATED APPLICATIONS

This application is related to and is a continuation in part of co-pending U.S. application Ser. No. 10/202,957, filed Jul. 25, 2002, and U.S. application Ser. No. 10/292,338, filed Nov. 12, 2002, and provisional U.S. Application No. 60/681,693, filed May 17, 2005, each of which applications is incorporated herein by this reference.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

The present invention relates generally to the field of medicine and, more particularly, to prevention and treatment of diseases or conditions associated with elevated levels of endogenous sodium pump inhibitors, including, without limitation, the pregnancy-related conditions known as gestational hypertension, preeclampsia, eclampsia and intrauterine growth restriction.

2. Related Art

Conception results from the fertilization of an egg by a sperm and the development of the resulting embryo into a fetus. In order for pregnancy to be established and the embryo to develop it must embed itself within the uterine wall. At about 12 weeks' gestation a temporary disk-shaped organ forms (the placenta), enhancing the transfer of oxygen and nutrients to, and permitting the removal of waste products from, the fetus. The placenta is critical to fetal development, and improper placental formation is associated with preeclampsia and intrauterine growth restriction.

Upon conception, the fertilized egg (embryo) undergoes repeated cell division and cell migration to form a blastocyst, a single layer of cells surrounding a central cavity. One area of the blastocyst wall that is three or four cells thick, known as the embryonic pole, becomes recognizable as the embryo and eventually develops into the fetus. The remaining blastocyst cells form a structure called the trophoblast. Pregnancy begins upon implantation of the blastocyst. Implantation occurs when the trophoblasts proliferate and invade the uterine wall so that the blastocyst burrows into the central layer of tissue (endometrium). The trophoblasts then develop to form the chorion (outer membrane) and amnion (inner membrane) surrounding the embryo. The amniotic sac fills with fluid and expands to envelop the embryo. The embryo continues to grow but is confined within one wall of the uterus until about the 12th week of gestation. At that time, the endometrium tissue overlying the embryo comes in such close contact with the tissue of the opposite uterine wall that they fuse and obliterate the endometrial cavity. The only cavity that remains in the uterus is the amniotic cavity, containing amniotic fluid and the fetus.

Placentation begins at about 10 days' gestation, when the trophoblasts invade the endometrium and its blood vessels (spiral arterioles). As early as day 11 or 12, branch-like cell formations (villi) begin to form on the chorionic surface. Invasion of the maternal spiral arterioles causes maternal blood to leak into spaces between the villi, providing nourishment to the developing embryo. At about 12 weeks' gestation, the placenta begins to form as a distinct, disk-shaped organ. The placenta is attached by the villi to the decidua directly overlying maternal spiral arterioles. The maternal spiral arterioles empty maternal blood into the intervillous space so that the blood circulates around and through the latticework of villi. Nutrients are transferred from maternal blood in the intervillous space, across trophoblast cells, through the fibrous core of the villus, and through the endothelial cells of the fetal capillaries to the fetal blood. Fetal wastes move in the opposite direction. The placenta reaches its final development at approximately 18 to 20 weeks' of pregnancy.

It is generally known that abnormal placentation and placental vascular insufficiency are central features of certain pregnancy-related medical conditions, including, without limitation, preeclampsia and intrauterine growth restriction. Preeclampsia is a rapidly progressive condition, characterized by the occurrence of high blood pressure and abnormal levels of protein in the urine (proteinuria). Eclampsia is a more severe form of preeclampsia that is also characterized by seizures. Gestational hypertension is hypertension in pregnancy without proteinuria, and it may be a less severe form of or a precursor to preeclampsia. Preeclampsia and gestational hypertension may be further classified as mild or severe depending upon the severity of the clinical symptoms. These hypertension-related disorders are collectively referred to herein as "pregnancy-induced hypertension" or "PIH."

Typically, clinical symptoms of PIH occur in the late second trimester or in the third trimester of pregnancy, although symptoms may occur earlier in pregnancy. PIH may be superimposed over other forms of hypertension, such as essential and secondary hypertension, that exist prior to or develop early in pregnancy. An increased risk for PIH is associated with first time pregnancies, when there is a large interval between pregnancies, pregnant women under the age of 20 or over the age of 35, women of black race, multi-gestational pregnancies, women who have conceived through in vitro fertilization ("IVF"), women who have had a prior pregnancy with PIH, women who have had a prior pregnancy conceived with a different partner, women with a family history of PIH or high blood pressure or diabetes, women who are of higher than normal weight or body mass index prior to pregnancy, undernutrition, women with a personal history of polycystic ovarian syndrome, insulin resistence or diabetes, hypertension, renal (kidney) disease, rheumatoid arthrisis, systemic lupus erythematosus or other autoimmune diseases, or thrombophilia risk factors. The risk of recurrent PIH in subsequent pregnancies is approximately thirty-three percent (33%), and PIH is superimposed in twenty-five percent (25%) of pregnancies in which chronic hypertension is present before pregnancy.

It is believed PIH occurs in five percent (5%) to ten percent (10%) of all human pregnancies. PIH disorders are a leading global cause of maternal and infant illness and death. PIH occurs in over six million births a year and is responsible for 15 percent of all premature births. By conservative estimates, these disorders are responsible for 76,000 deaths each year. The risk of death for a pregnant woman with severe preeclampsia is 0.5%, and the risk of perinatal death for her baby is 13%; if the condition remains untreated and eclampsia develops, the risk of maternal and fetal death increases to 5% and 28%, respectively. Zupan J., Perinatal Mortality in Developing Countries, *New Engl J. Med.* 352(20) 2047-248 (2005).

PIH is a syndrome having maternal and fetal manifestations. The maternal condition is characterized by vasospasm, activation of the coagulation system, oxidative stress and inflammatory-like responses, all of which have detrimental effects on the placenta, kidney, blood, liver, vasculature, cardiopulmonary system and brain. PIH is a systemic syndrome, and several of its non-hypertensive symptoms and complications may be life-threatening even with only mild increases in blood pressure.

Intrauterine growth restriction or retardation ("IUGR") and intrauterine fetal demise are fetal symptoms of or complications associated with PIH. IUGR is the second leading cause of perinatal morbidity and mortality, and it occurs in approximately 5% of the general obstetric population. Placental insufficiency, preeclampsia and abnormal placentation are generally recognized by those skilled in the art as being among the causes of or contributory factors in IUGR.

Women who develop mild gestational hypertension after 37 weeks' gestation have pregnancy outcomes similar to those of pregnant women who are normotensive, apart from increased rates of induced labor and cesarean delivery. Conversely, women with severe gestational hypertension have high rates of placental abruption, preterm delivery and small-for-gestational-age babies (the postnatal counterpart and likely result of IUGR) similar to those of women with severe preeclampsia. Twenty-five percent (25%) of cases of eclampsia occur postpartum, usually in the first 2 to 4 days after delivery.

After a diagnosis of severe PIH, the baby is generally induced and delivered if it is near term, i.e., after 36 weeks. However, if PIH occurs earlier in the pregnancy, its impact is more profound because fetal viability is low; infant death occurs in approximately 87% of these cases. For pregnancies in which PIH occurs earlier than 24 weeks, the induction of labor is recommended and results in essentially 100% neonatal mortality. For pregnancies between 24 and 28 weeks' gestation, management of PIH may be attempted to increase gestational age, provided that there is close monitoring for maternal and fetal complications. Regardless of gestational age of the fetus, delivery is the management method of choice for eclampsia.

To date, there is no cure or effective treatment for PIH or IUGR. Delivery of the baby and placenta usually resolves the maternal symptoms of PIH within twelve (12) weeks' postpartum. However, if the baby is not near term then early delivery is generally contrary to the best interests of the baby. Prophylactic measures against PIH, including calcium supplementation, vitamin and antioxidant supplementation and aspirin therapy, have not proven to be successful.

Depending upon the stage of the pregnancy and the severity of maternal and fetal conditions, gestational hypertension, preeclampsia, eclampsia, and IUGR may be managed in an attempt to prolong the pregnancy and advance the gestational age to improve the fetal outcome. If maternal symptoms persist after delivery, management of PIH symptoms is necessary to prevent deterioration of the maternal condition or further development of complications.

Traditional management of PIH includes bed rest and antihypertensive and/or anticonvulsant therapy, including, without limitation, hydralazine, nifedipine, sodium nitroprusside, 1-methyldopa (e.g., Aldomet®), atenolol, labetalol, magnesium sulfate and phenytoin. Management of IUGR includes treatment of the concomitant maternal disease (e.g., gestational hypertension or preeclampsia) and bed rest. Preterm delivery may be necessary to prevent intrauterine demise due to chronic fetal oxygen deprivation or if the maternal condition does not respond to management efforts.

The cause(s) of PIH and IUGR remain elusive. The extensive list of possible causes currently being investigated by those skilled in the art include (1) immunologic factors (maternal reaction to paternal antigen or circulating auto-antibodies that activate angiotensin II), (2) genetic factors, (3) insulin resistance and increased levels of insulin, free fatty acids and triglycerides, (4) dietary calcium deficiency, (5) increased oxidative stress, (6) prostaglandin imbalance (increased ratio of thromboxane to prostacyclin), and (7) circulating pro-angiogenic factors and their inhibitors (e.g., soluble fms-like tyrosine kinase 1, an agonist of vascular endothelial growth factor and placental growth factor). Roberts J M and Gammill H S, Preeclampsia Recent Insights, *Hypertension* (December 2005) 1243-1249; Noris M, et al., Mechanisms of Disease: Preeclampsia, *Nature of Clinical Practice Nephrology* 1(2): 98-110 (December 2005); Solomon C G and Seely E W, Preeclampsia—Searching for the Cause, *N. Engl. J. Med.* 350(7):641-642 (2004); Davison, J M, et al., New Aspects in the Pathophysiology of Preeclampsia, *J. Am. Soc. Nephrol.* 15:2440-48 (2004); Pridjian G and Puschett J B, Preeclampsia Part 2: Experimental and Genetic Considerations, *Obstet. Gynecol. Survey* 57(9):619-634 (2002)(summarizing early research to determine the role of endogenous digitalis-like factors in preeclampsia and concluding that results are unclear).

Notwithstanding the state of the art and various popular theories being investigated by others in the field, it is theorized by Applicant that certain endogenous "digoxin-like" factors originating from maternal, placental and/or fetal sources may be a cause of or a contributing factor in these conditions. Serum of adult patients in renal or liver failure, pregnant women, neonates and umbilical cord blood evidence endogenous factors that cross-react with anti-digoxin antibodies when assayed with commercially available immunoassays for digoxin. Some, but not all, studies have shown that these endogenous factors are present at higher levels in women with preeclampsia than in women without preeclampsia.

These endogenous factors have generally been referred to as endogenous "digoxin-like," "digitalis-like," "endoxin," "endobain," "sodium pump inhibitors" or "sodium pump ligands" not only because they cross-react with digoxin antibodies, but because they are also known to inhibit activity of sodium/potassium ATPase in vitro. Certain known exogenous sodium pump inhibitors belong to classes of compounds known as cardenolides and bufadienolides, commonly referred to as cardiotonic steroids or cardiac glycosides. The aglycone moieties of cardenolides and bufadienolides are also known to be sodium pump inhibitors. Pullen M A, et al., Characterization of the Neutralizing Activity of Digoxin-Specific Fab Toward Ouabain-like Steroids, *J. Pharm. and Exp. Therapeutics* 310(10): 319-325 (2004).

For the better part of a generation, the possible role of these endogenous factors in PIH and IUGR has been generally discounted or discredited by leading investigators in the field, who found that there was no difference between levels of endogenous factors in women with and without preeclampsia and who, therefore, concluded that endogenous factors are not predictive of and do not play a major role in preeclampsia. See, Gonzales, A R, et al., Digoxin-like Immunoreactive Substance in Pregnancy, *Am. J. Obstet. Gynecol.* 157(3):660-664 (1987); Phelps, S J, et al., The Influence of Gestational Age and Preeclampsia on the Presence and Magnitude of Serum Endogenous Digoxin-like Immunoreactive Substance(s),

*Am. J. Obstet. Gynecol.* 158(1): 34-39 (1988). Thus, endogenous factors are not among the models of PRI or IUGR being currently suggested or investigated by other researchers generally skilled in the art. Roberts J M and Gammill H S, Hypertension (December 2005) 1243-1249; Noris M, et al., *Nature of Clinical Practice Nephrology* 1(2): 98-110 (December 2005); Solomon C G and Seely E W, *N. Engl. J. Med.* 350(7):641-642 (2004); Davison, J M, et al., *J. Am. Soc. Nephrol.* 15:2240-48 (2004); Redman C W, Sargent I L, Latest Advances in Understanding Preeclampsia, *Science* 308 (5728):1592-94 (2005); Pridjian G and Puschett J B, *Obstet. Gynecol. Survey* 57(9):619-634 (2002).

Applicant has discovered that symptoms of PIH and IUGR may be due, in whole or in part, to inhibition of the sodium pump by endogenous factors. It is theorized by Applicant that a decrease in sodium pump activity, particularly in vascular endothelial cells, may cause an increase in intracellular sodium and calcium ions, promoting vasoconstriction, vasospasm and the resultant hypertension found in PIH. Furthermore, in placental cells, many nutrient transport processes are coupled to $Na^+$ transport and energized by the $Na^+$ gradient. Thus, Applicant believes that inhibition of the sodium pump by these endogenous factors may also impair nutrient and oxygen supply to the placenta, restrict nutrient and blood flow to the developing fetus, and limit the removal of metabolic waste products from the fetus—all of which cause or contribute to IUGR.

It is known that, in vitro, sodium pump inhibition by endogenous factors may be reversed or prevented by addition of antibodies to cardenolides and bufadienolides, particularly digoxin immune Fab. Pullen M A, et al., *J. of Pharm. and Exp. Therapeutics* 310(10): 319-325 (2004). As disclosed in the prior and co-pending U.S. application Ser. Nos. 10/202,957, 10/292,338, and 60/681,693, Applicant has discovered that antibodies to cardenolides and bufadienolides are useful in diagnosing and/or treating the causes, symptoms and/or complications of PIH and IUGR.

Determination of an effective antibody composition requires, inter alia, a determination of the body load of antigen that must be neutralized by the antibody. There is no known available immunoassay specific for the endogenous factors that Applicant believes cause or contribute to PIH and IUGR. However, commercially available immunoassays have been developed to detect digoxin, ouabain and marinobufagenin. Commercially available immunoassays for exogenous cardiac glycosides (particularly, immunoassays for digoxin, oubain and marinobufagenin) that have been used to detect serum levels of endogenous factors in pregnant women with and without preeclampsia, have detected the following levels of endogenous factors: <0.1 to 1.5 ng/mL, "digoxin"; 0.54 to 0.86 nmol/L, "ouabain"; and 2.53 to 2.73 nmol/L "marinobufagenin." Lopatin D A, et al., Circulating Bufodienolide and Cardenolide Sodium Pump Inhibitors in Preeclampsia, *J. Hypertension* 17(8): 1179-1187 (1999); Adair C D, et al., Elevated Endoxin-Like Factor Complicating a Multifetal Second Trimester Pregnancy: Treatment with Digoxin-Binding Immunoglobulin, *Am. J. Nephrol.* 16:529-531 (1996); Seely E W, et al., Markers of Sodium and Volume Homeostasis in Pregnancy-Induced Hypertension, *J. Clin. Endocrinol. Metabol.* 74(1): 150-156 (1992); Craig H R, et al., Binding of Endogenous Digoxin-like Immunoreactive Factor to Serum Proteins During Normal and Hypertensive Pregnancy, *J. Clin. Immunoassay* 14(4): 245-250 (1991); Goodlin R C, Antidigoxin Antibodies in Eclampsia, *N. Engl. J. Med.* 618(8): 518-519 (Feb. 25, 1988); Goodlin R C, Will Treatment with Digoxin Antibody Benefit Pregnant Patients with Toxemia and Elevated Digoxin Like Factor?, *Medical Hypothesis* 24:107-110 (1987); Beyers A D, et al., The Possible Role of Endogenous Digitalis-like substance in the Causation of Pre-eclampsia, *SA Medical Journal,* 65: 883-885 (1984); Gusdon J P, et al., A Digoxin-like Immunoreactive Substance in Preeclampsia, *Am. J. Obstet. & Gynecol.* 150:83 (1984); Graves S W and Williams G H, An Endogenous Ouabain-like Factor Associated with Hypertensive Pregnant Women, *J. Endocrinol. Metab.* 59:1070 (1984).

However, it is also known that there is variation among immunoassays in detecting endogenous "digoxin-like" factors. Furthermore, a number of substances such as steroids, lipids and bile are known to cross-react with anti-digoxin antibodies and may interfere with detection of endogenous factors in patients who have not been treated with digoxin or digitalis. Ghione S, et al., Endogenous Digitalis-like Activity in the Newborn, *J. Cardio. Pharmacol.* 22: S25-S28 (1993); McMillan G A, et al., Comparable Effects of Digibind and DigiFab in Thirteen Digoxin Immunoassays, *Clin. Chemistry* 48(9): 1580-84 (2002); Pudek M R, et al., Seven Different Digoxin Immunoassay Kits Compared with Respect to Interference by a Digoxin-Like Immunoreactive Substance in Serum from Premature and Full Term Infants, *Clin. Chem.* 29(11): 1972-1974 (1983).

Thus, Applicant believes that immunoassays specific for exogenous cardenolides or bufadienolides, including digoxin immunoassays, have not accurately detected the levels of endogenous factors in pregnant patients. It is believed that a substantial portion of endogenous factors, perhaps up to 90%, are protein-bound and not detectable by direct measurement with conventional immunoassay techniques. Valdes R, Graves S W, Protein binding of Endogenous Digoxin-immunoactive Factors in Human Serum and its Variation with Clinical Condition, *J. Clin. Endocrinol. Metabol.* 60:1135-1143 (1985). This is further evidenced because sodium pump inhibition by endogenous factors substantially exceeds that which would be expected based upon the levels of endogenous factors detected by conventional immunoassay. Pullen M A, et al., *J. of Pharm. and Exp. Therapeutics* 310(10): 319-325 (2004).

The discrepancy in immunoassay measurements of endogenous factors and lack of concordance with sodium pump inhibition suggests that there are differences between endogenous factors and exogenous cardenolides and bufadienolides. Miyagi H, et al., Ouabain-like Na/K-ATPase Inhibitory Activity of a Plasma Extract in Normal Pregnancy and Pregnancy Induced Hypertension, *Japan. J. Pharmacol.* 57: 571-581 (1991). Thus, it is theorized by Applicant that the endogenous factors are not digoxin, ouabain, bufalin, marinobufagenin or other known exogenous cardenolides and bufadienolides, but are one or more compounds that differ in biological, chemical, physical, biopharmaceutical and/or pharmacokinetic characteristics from exogenous cardiac glycosides.

Applicant has discovered that if antibodies to exogenous cardenolides and bufadienolides are to be useful in diagnosing, preventing and/or treating PIH and IUGR, an effective antibody composition may not be determined solely upon measurements of endogenous factors resulting from immunoassays specific for exogenous cardiac glycosides, such as digoxin, ouabain, bufalin or marinobufagenin.

Except as described in related U.S. application Ser. Nos. 10/202,957, 10/292,338, and PCT/US2003/023235, WO 2004/011028 A1 (each of which applications is incorporated herein by this reference), there is no known efficacious composition of antibodies that bind digoxin (including any other exogenous cardenolide or bufadienolide that is not specific for digoxin), or method of using such antibody compositions, for predicting, preventing, diagnosing or treating gestational hypertension, preeclampsia, eclampsia or intrauterine growth restriction.

Goodlin (1988) and Adair, et al. (1996) have investigated the effects of digoxin antibodies on preeclampsia in vivo. These investigators administered antibody compositions based upon measured serum digoxin concentrations, doses and standard dosing formulas for treating digoxin intoxication. These initial experiments failed to establish digoxin antibody compositions that were effective for treating the symptoms of preeclampsia, extending pregnancy or advancing fetal development.

In the first experiment, Goodlin intravenously administered 10 mg total digoxin antibodies to a preeclamptic patient having a serum endogenous factor level of 0.3 ng/mL (as determined by digoxin immunoassay). The 10 mg composition was repeated once after 12 hours. Each antibody composition administered to the patient produced a precipitous, albeit transient, reduction in mean blood pressure. The patient's blood pressure began to rise approximately one hour after each antibody composition was administered. Goodlin did not report the reduction in mean blood pressure to be statistically significant. Furthermore, the results cannot be attributed solely to administration of digoxin antibodies because of the concurrent intravenous administration of antihypertensive drugs and albumin. Goodlin states that the increase in urinary output was due, in part, to concurrent administration of albumin. However, Goodlin did not address the synergistic or combined effects of the antihypertensive drug administration in combination with digoxin antibodies. Regrettably, and most significantly from a scientific and medical perspective, the pregnancy was terminated prematurely and the fetus did not survive. Goodlin R C, *New Engl. J. Med.* 618(8): 518-519 (1988).

In the second experiment, Adair, et al., administered a single composition of 29 mg total digoxin antibodies to a patient (twin gestation) exhibiting a serum endogenous factor level of 0.4 ng/mL (as determined by digoxin immunoassay). The composition was given as a partial bolus (5 mg) and a slow infusion at a rate of 1 mg/hour for 24 hours. Although mean arterial pressure gradually declined until approximately 12 hours after the treatment commenced, the reduction was not statistically significant. Moreover, during digoxin antibody treatment the patient exhibited more than a two-fold increase in proteinuria. The worsening proteinuria led to premature termination of the pregnancy and, as in Goodlin, neither of the fetuses survived. Adair C D, et al., *Am. J. Nephrology* 16:529-531 (1996). Thus, neither Goodlin nor Adair established an antibody composition that was therapeutically effective for treating preeclampsia.

Endogenous factors may also cross-react with antibodies specific for other non-digoxin cardenolides or bufadienolides, such as bufalin, ouabain or marinobufagenin. PCT US 2004/002802, WO 2004/071273 A2 (republished WO 2004/071273 A3) (incorporated herein by this reference), claims that increasing urinary levels of marinobufagenin are a diagnostic indicator of preeclampsia. This patent application has also generally suggested that antibodies to marinobufagenin may be used to treat preeclampsia. However, patent application WO 2004/071723 does not teach a therapeutically effective composition or dosing administration regimen for treating preeclampsia with marinobufagenin antibody.

To date, PIH is believed to be a condition specific to humans. Thus, there is no known naturally occurring animal model of PIH available for the study of gestational hypertension, preeclampsia or eclampsia. Recently, some investigators have attempted to create an animal model by administering a high salt diet to pregnant rats and suggesting that pregnant rats on the high salt (NaCl) diet exhibit symptoms of "preeclampsia." It has been shown that an antibody to marinobufagenin lowers blood pressure in the pregnant rats on high NaCl intake. Fedorova et al., Antibody to Marinobufagenin Lowers Blood Pressure in Pregnant Rats on a High NaCl Intake, *J. Hypertension* 2005: 23(4):835-842. However, this proposed animal model has substantial differences from naturally occurring preeclampsia in humans. For example, the manner of trophoblast invasion and placentation are significantly different between rats and humans. The mild increase in urinary protein in the rats does not approach significant proteinuria (>300 mg/24 hours) that evidences preeclampsia in humans. Furthermore, the results of the antibody "treatment" are suspect because the treatment was with whole antibody and not Fab fragments. Therefore, the resulting reduction in blood pressure in rats may be due, in whole or in part, to an allergic or immune reaction to whole antibody instead of a "binding-inactivation" of the endogenous factor by the antibody. Another major difficulty in designing or evaluating a study involving an animal model of preeclampsia relates to the manipulation and intervention to which the animal is subjected. This includes a number of factors such as the handling of the animals, the route of administration of any agent, and the methods used to measure the different variables, particularly blood pressure. Most methods for measuring blood pressure require restraining or tethering the animal which could lead to artificial elevation of blood pressure, especially in cases where compensatory mechanisms have been eliminated. The effect of stress in the animals caused by the required manipulation, in and of itself, has been clearly shown to result in changes which could mimic preeclampsia. Thus, this recently proposed animal model has not proven to be an accurate model of true preeclampsia and has not been generally accepted for the study of preeclampsia.

Applicant has disclosed in related U.S. application Ser. No. 10/202,957 that administering anti-digoxin antibodies to preeclamptic women mitigates or reverses the symptoms or complications of PIH and IUGR. It is believed that by mitigating or reversing the symptoms or complications of PIH, PIH and IUGR will be controlled, the pregnancy may be extended and fetal development may be advanced. Also, in related U.S. application Ser. No. 10/292,338 and PCT/US2003/023235, WO 2004/011028 A1 it has been further disclosed that antibodies to digoxin may be used to control or regulate, inter alia, $Na^+/K^+$ ATPase, to improve maternal blood flow, nutrient exchange and metabolic waste removal between the maternal vasculature and the placenta and fetus, and to prevent or limit IUGR.

The present invention is directed to overcoming one or more of the problems set forth above, including overcoming the lack of a pharmaceutical composition that is effective for preventing or treating one or more causes, symptoms or complications of PIH or IUGR, that does not have adverse side effects, and that prolongs a PIH or IUGR pregnancy to allow further development of the fetus. It would be particularly beneficial for pregnancy to be prolonged for a period of time sufficient to administer therapeutically effective doses of corticosteroids or other pharmaceutical compositions that either advance fetal organ development or that prevent or limit the adverse physical consequences in the neonate that may be due, in whole or in part, to premature delivery. It would also be beneficial to have a pharmaceutical composition that is effective for treating one or more causes, symptoms or complications of PIH that occur or persist after delivery of the fetus, and particularly for treating symptoms or complications of PIH that are not managed by or responsive to traditional antihypertensive drugs or anti-convulsant or other agents used to manage seizures, HELLP, ocular or neurological deficits or disturbances, or any other symptom or complication of PIH that develops or continues postpartum.

Because the specific etiologies of gestational hypertension, preeclampsia, eclampsia and intrauterine growth restriction remain elusive, the medical definitions or diagnostic indicators of these conditions continue to be revised from time to time. Thus, any conventional diagnostic or prognostic method for assessment of the risk of or determining the presence of chronic or essential hypertension, gestational hypertension, preeclampsia, eclampsia or IUGR may be used in connection with the invention. The inventions described herein are not limited in any manner by the descriptions, definitions, diagnostic or clinical indications of PIH or IUGR described herein, and are deemed to include all existing and future revisions to the medical definitions or diagnostic or prognostic indicators of gestational hypertension, preeclampsia, eclampsia, any other form of hypertension exhibited during pregnancy, and intrauterine growth restriction.

BRIEF SUMMARY OF THE INVENTION

Pregnant women experiencing PIH or IUGR have serum levels of one or more endogenous factors that are detectable by immunoassay for digoxin—a component of digitalis that is only found in certain plants. The endogenous factors are present even though these pregnant women have not been poisoned or treated with digitalis. Because these endogenous factors are not digoxin, anti-digoxin antibody treatment for digoxin poisoning is not indicated for pregnant women. Furthermore, even if the endogenous factors in pregnant women were digoxin, pregnant women do not exhibit levels that warrant digoxin antibody treatment. The endogenous factors in pregnant women, as measured by digoxin immunoassay, are detected in the range of $\leqq 0.1$ ng/mL to 1.5 ng/mL. These endogenous factor levels are substantially lower than the serum digoxin levels which are classified as life-threatening digoxin toxicity (i.e., greater than 6 ng/mL). Thus, one of ordinary skill in the art would not treat pregnant women with digoxin antibodies to counteract these low levels of endogenous factors.

However, Applicant has surprisingly discovered that symptoms of PIH and IUGR may be effectively treated with high dose digoxin antibody compositions. When presented herein in quotation marks, the term "digoxin" (e.g., serum "digoxin" concentration) means one or more endogenous factor(s) that are detectable by an immunoassay for digoxin. Digoxin antibody compositions that are effective to treat PIH and IUGR have digoxin binding capacity that is greater than the digoxin binding capacity that would be used to treat the serum "digoxin" concentrations observed in pregnancy if the endogenous factors were, in fact, digoxin and if comparable digoxin concentrations were deemed to be so poisonous or toxic as to justify digoxin antibody treatment.

Accordingly, the present invention relates to a pharmaceutical composition for preventing, limiting the effects of, delaying the onset of, or treating one or more of the causes, symptoms or complications of gestational hypertension, preeclampsia, eclampsia or intrauterine growth restriction. The invention also relates to a method of preventing, limiting the effects of, delaying the onset of, or treating gestational hypertension, preeclampsia, eclampsia or intrauterine growth restriction by administrating to a mammal a pharmaceutical composition having a high dose of digoxin binding capacity.

In one aspect of the invention, the pharmaceutical composition comprises an antibody that reacts immunologically with or otherwise binds digoxin or digitoxin, having an active ingredient comprising a level of digoxin binding capacity that is greater than the digoxin binding capacity that would be administered to neutralize digoxin or digitoxin toxicity in a subject having substantially the same serum digoxin concentration as the serum "digoxin" concentration observed in pregnant women (i.e., a high dose digoxin antibody composition).

The invention further relates to a pharmaceutical composition having a therapeutically effective amount of digoxin binding capacity (the active ingredient) sufficient to treat at least one cause, symptom or complication of PIH or IUGR. In one aspect of the invention, the composition has a therapeutically effective amount of the active ingredient to reduce systolic blood pressure, diastolic blood pressure or mean arterial pressure. In another aspect of the invention, the composition comprises a therapeutically effective amount of the active ingredient sufficient to cause a decrease in proteinuria. The invention also relates to a composition having a therapeutically effective amount of the active ingredient sufficient to cause an increase in urinary output, an increase in creatinine clearance, or a reduction in serum creatinine concentration. The invention also relates to a composition having a therapeutically effective amount of digoxin binding capacity sufficient to cause a decrease in peripheral, cerebral or pulmonary edema. The invention also comprises a composition having a therapeutically effective amount of digoxin binding capacity sufficient to cause an improvement in one or more neurological parameters, including, without limitation, clonus, hyper reflexia, central nervous system irritability, headache, eclamptic seizure, ocular function (e.g., scotomata, double vision (diplopia), blurred vision, photophobia retinal detachment, amaurosis and blindness), and fetal peri ventricular or intraventricular hemorrhage.

The invention also relates to a composition having a therapeutically effective amount of digoxin binding capacity sufficient to cause an increase in blood flow through a vein or artery, preferably a middle cerebral artery flow (maternal or fetal) or an umbilical artery or umbilical vein. The invention also relates to a therapeutically effective digoxin antibody composition sufficient to increase nutrient delivery, oxygenation, metabolic waste removal or fluid exchange between the maternal circulation and the placenta and/or a fetus at risk for developing or exhibiting intrauterine growth restriction.

The invention also comprises a composition having a therapeutically effective amount of digoxin binding capacity sufficient to reduce or reverse inhibition of the sodium pump, or increase sodium pump activity, in the cells of a mammal exhibiting gestational hypertension, preeclampsia, eclampsia or intrauterine growth restriction.

The invention further relates to a composition comprising a therapeutically effective amount of digoxin binding capacity sufficient to cause a clinically beneficial reduction in systolic or diastolic blood pressure, mean arterial pressure, creatinine clearance, urinary output, serum creatinine levels, or proteinuria. The invention further relates to a composition comprising a therapeutically effective amount of digoxin binding capacity sufficient to cause a statistically significant reduction in systolic or diastolic blood pressures, mean arterial pressure, serum creatinine level or proteinuria, or a statistically significant improvement in urinary output or creatinine clearance.

The invention also relates to a method of preventing, limiting the effects of, delaying the onset of, or treating gestational hypertension, preeclampsia, eclampsia or intrauterine growth restriction, including the step of administering to a patient at risk for developing or suffering from one or more symptoms of PIH or IUGR, a composition of antibody that reacts immunologically with or otherwise binds digoxin, the composition having as the active ingredient digoxin binding capacity greater than that which would be given to neutralize digoxin intoxication in a mammal having substantially the same serum digoxin concentration as the serum "digoxin" concentration observed in pregnant women. The method may further include the step of administering multiple compositions having different therapeutically effective amounts or repeated administration of a composition having the same or a different therapeutically effective amount of the active ingredient.

These aspects are merely illustrative of the innumerable aspects associated with the present invention and should not be deemed as limiting in any manner. These and other aspects, features and advantages of the present invention will become apparent from the following detailed description when taken in conjunction with the drawings. Although methods and materials similar or equivalent to those described herein may be used in the practice of the present invention, suitable methods and materials are described below. In addition, the materials, methods and examples are illustrative only and not intended to be limiting in any manner.

DETAILED DESCRIPTION OF THE INVENTION

I. Definitions and Abbreviations

Figure 1:
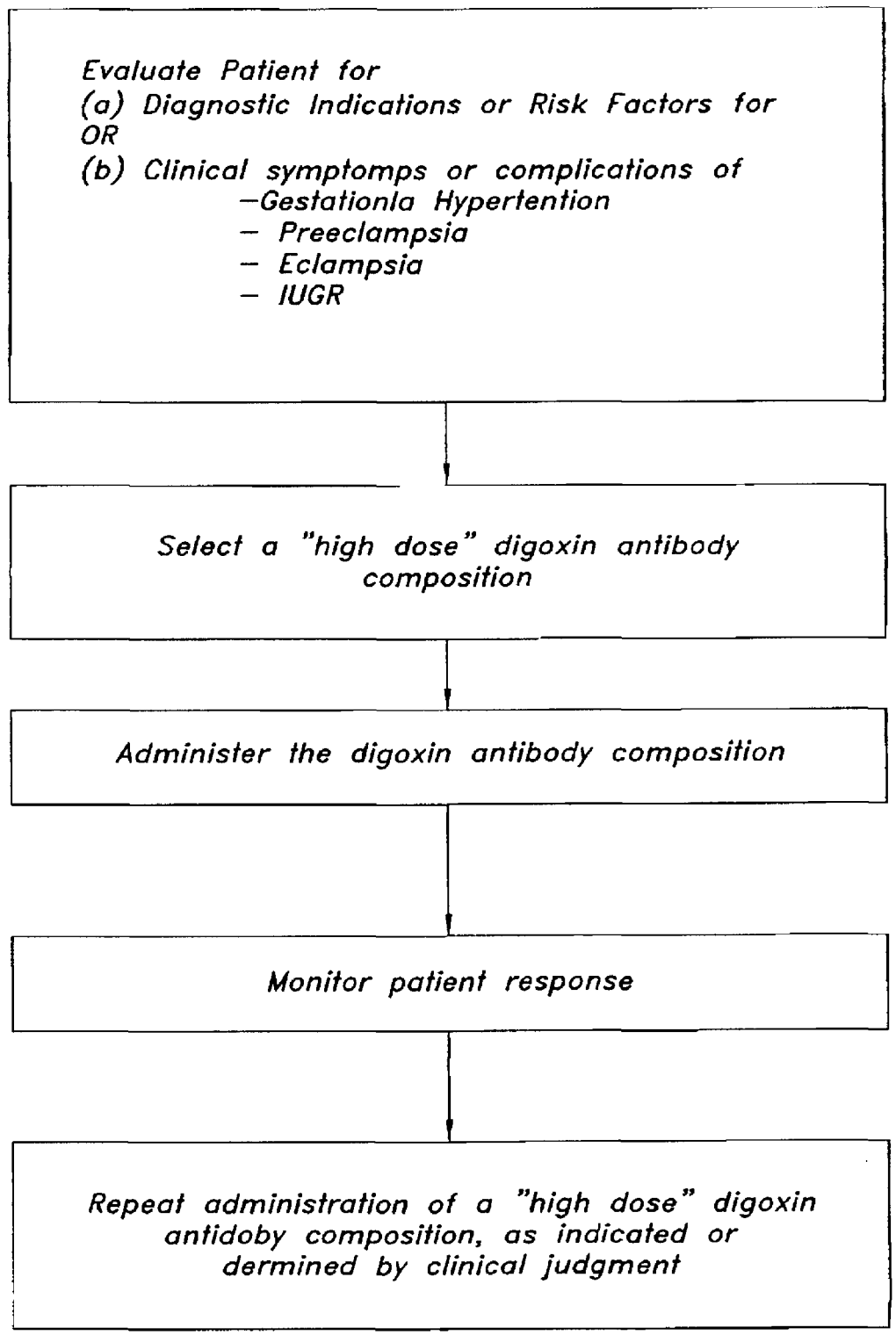
FIG. 1 is a flow chart illustrating the steps and sequence of a method for treating gestational hypertension, preeclampsia, eclampsia or intrauterine growth restriction.

The following terms as used herein shall have the definitions set forth below. When such terms are used in the context as defined below, then such terms may be used in the abbreviated form set forth adjacent to such term.

"pregnancy-induced hypertension" or "PIH" mean and include one or more of non-proteinuric gestational hypertension, preeclampsia and eclampsia, and include such conditions when occurring antepartum (whether before or after 20 weeks' gestation) or postpartum. PIH may be superimposed over other forms of hypertension, such as chronic or essential or secondary hypertension. Accordingly, for purposes of the invention PIH includes any form of hypertension when present during pregnancy. When PIH is superimposed over existing forms of hypertension the prognoses for mother and fetus are much worse than either condition alone. Superimposed PIH is the likely diagnosis (1) where new onset proteinuria occurs when non-proteinuric hypertension is present early in pregnancy (before 20 weeks' gestation), and (2) in women with hypertension and proteinuria before 20 weeks' gestation if there is thrombocytopenia (platelet count$\geq$50,000/mm$^3$ and $\leq$100,000 cells/mm$^3$), increase of alanine or aspartate aminotransferase or alkaline phosphatase (together, "liver enzymes") to abnormal levels, sudden increase in proteinuria, or sudden increase in blood pressure where hypertension has previously been well controlled. Furthermore, any pregnant woman whose blood pressure increases by 30 min Hg systolic or 15 mm Hg diastolic (even if it does not exceed 140 mm Hg systolic or 90 mm Hg diastolic) may be considered to have PIH. Additional symptoms and complications of PIH may include: peripheral edema; exaggerated myocardial function, vasoconstriction and vasospasm; eclamptic seizures; hemolysis, elevated liver enzyme levels and low platelets (when occurring together, referred to as HELLP syndrome); hepatic rupture, elevated blood urea nitrogen ("BUN") or bilirubin or lactate dehydrogenase ("LDH"); pulmonary edema; acute renal failure; placental abruption; IUGR or intrauterine fetal demise; cerebral edema and cerebral hemorrhage (including fetal periventricular and intraventricular hemorrhage); scotomata, double or blurred vision, amaurosis, cortical blindness, retinal detachment; and neurological disturbances (headache, altered consciousness or mental status, hyper reflexia, central nervous system irritability, clonus).

"proteinuria" means the urinary excretion of at least 0.3 gm protein in a 24-hour specimen, which usually correlates with at least 30 mg/dL ($\geq$1+ on dipstick), with no evidence of urinary tract infection.

"gestational hypertension" means non-proteinuric hypertension during pregnancy. Gestational hypertension is generally characterized as the acute onset of hypertension in pregnancy or the early puerperium without proteinuria. Gestational hypertension usually resolves within ten (10) days after delivery. Currently, a diagnosis of gestational hypertension requires a blood pressure of at least 140 mm Hg systolic or 90 mm Hg diastolic measured at least two times and at least six hours apart, that develops after 20 weeks' gestation in a previously normotensive patient. Sustained blood pressure measurements over 160 mm Hg systolic or 110 mm Hg diastolic are classified as severe gestational hypertension.

"preeclampsia" means the occurrence of high blood pressure and proteinuria during pregnancy (usually after 20 weeks' gestation). Preeclampsia is further characterized as either mild or severe. Currently, the American College of Obstetricians and Gynecologists ("ACOG") defines mild preeclampsia as the occurrence in pregnant women of hypertension greater that 140 mm Hg systolic or 90 mm Hg diastolic and proteinuria greater than 300 mg per 24 hours. ACOG currently defines severe preeclampsia as preeclampsia with one or more of the following: (1) hypertension greater than 160 mm Hg systolic or 110 mm Hg diastolic, as measured on two occasions at least six hours apart while on bed rest, (2) a proteinuria level of greater than 500 mg per 24 hour period or 3+ or greater on two random urine samples collected at least 4 hours apart, (3) thrombocytopenia (platelets$\geq$50,000/mm$^3$ and $\leq$100,000/mm$^3$) or microangiopathic hemolysis, (4) elevations in alanine aminotransferase (ALT(SGPT)>72 U/L) or aspartate aminotransferase (AST(SGOT)>72 U/L), lactate dehydrogenase (LDH>600 U/L) or total bilirubin (>1.2 mg/dL), epigastric or right upper quadrant pain, (5) persistent headache or visual scotomata or other visual disturbances, (6) intrauterine growth restriction, (7) oliguria (urinary output less than or equal to 500 mL per 24 hours or average of $\leq$25 ml/hour over a 3 hour period), serum creatinine level of less than 1.2 mg/dL, or (8) pulmonary edema. Although not specifically included in the ACOG definition, general swelling or peripheral edema, especially when it occurs by rapid onset, may also indicate preeclampsia. Peripheral edema may be determined on a scale of 0 to 4+, with 0 representing no edema, 1+ barely detectable "pitting" or tissue indentation, 2+ "pitting" of <5 mm, 3+ "pitting" of 5-10 mm, and 4+ "pitting" of >10 mm. Peripheral edema is frequently evaluated in the leg, sacrum, hand, and face.

"eclampsia" means mild or severe preeclampsia together with seizures. Eclampsia may be further characterized by diminished or altered neurological function, mental status, severe agitation, confusion and unconsciousness for a variable period of time.

"intrauterine growth restriction" or "IUGR" mean intrauterine growth restriction or growth retardation of a fetus. IUGR is currently characterized by a fetus whose estimated weight is below the $10^{th}$ percentile for its gestational age and a maternal abdominal circumference below the 2.5 percentile for gestational age. IUGR may result in or contribute to intrauterine fetal demise. For purposes of the invention, to prevent, limit the effects of, or delay the onset of IUGR includes to prevent, limit the effects of, or to delay intrauterine fetal demise.

"sodium pump" or "sodium/potassium ATPase" or "$Na^+/K^+$ ATPase" mean the transmembrane protein that utilizes energy generated from adenosine triphosphate ("ATP") hydrolysis (ATP→ADP+$PO_4$) to transport sodium and potassium ions across cell membranes in opposite directions against their chemical and electrical gradients. The sodium pump is the primary transporter responsible for maintaining the electrochemical gradient of $Na^+$ across cell membranes and is important in regulating cell volume, cytoplasmic pH, $Na^+$-dependent glucose and amino acid transport, and regulating $Ca^{2+}$ levels through the $Na^+/H^+$ and $Na^+/Ca^{2+}$ ion exchange pumps. The sodium pump is regulated by multiple mechanisms in response to changes in cellular requirements or cellular environments.

"endogenous factors" or "EFs" mean those factors produced in a mammal that cross-react immunologically with antibodies to at least one cardenolide or bufadienolide. Sometimes herein, EFs are also referred to as digoxin-like substances ("DLS"), digoxin-like immunoreactive substances or factors ("DLIS" or "DLIF"), or endogenous digoxin-like factors ("EDLF").

"cardenolides (and/or) bufadienolides" or "cardiac glycosides" mean cardenolides and/or bufadienolides, and aglycones thereof, including, without limitation, digitalis, gitoxigenin, digoxigenin, digoxin, digitoxigenin, digitoxin, dihydrodigoxin, strophanthins, convallatoxin, cymarine, acetylstophanthidin, strophanthidin, ouabagenin, ouabain, dihydrooubain, neriifolin, proscillaridin, proscillaridin A, cinobufagen, cinobufatolin, marinobufagenin, norbufalin, bufanolide, bufalin and similar compounds, and their respective isomers, inotropes, congeners, variants, derivatives, equivalents, precursors and metabolites, and synthetic versions of any of the foregoing.

"therapeutically effective" means effective to treat a disease, syndrome or condition. As used herein, "treat" includes, without limitation, to prevent (prophylactic), reduce the severity of, control, limit the effects of, delay the onset of, alleviate or ameliorate one or more of the causes, symptoms, indications or complications of a disease, syndrome or condition. A therapeutically effective composition does not cause any unacceptable or significant adverse effect in the subject, including the worsening of any condition, complication or symptom to such an extent that the risks of the adverse effect outweigh the benefits to be derived from the treatment. A therapeutically effective composition may improve or stabilize one or more medical parameters that, in the absence of the composition, might otherwise worsen or develop into a symptom or complication of a disease, condition or syndrome.

"digoxin antibody" or "digoxin antibodies" mean an antibody or binding fragment that reacts immunologically with or binds to (either specifically or non-specifically) or contains a binding domain for digoxin, digitoxin, digitoxigenin, digoxigenin, or gitoxingenin. Digoxin antibodies may be specific to and include antibodies against any cardenolide or bufadienolide that has the ability to bind at least one epitope of digoxin or digitoxin, digitoxigenin, digoxigenin, or gitoxingenin. Digoxin antibodies include, without limitation, antibodies specific to digoxin, ouabain, bufalin, and marinobufagenin, or to a conjugate of any one of the foregoing. Digoxin antibodies also include calycin proteins, whether naturally occurring or wholly or partially synthetic or engineered, that are capable of binding digoxin, digitoxin, digitoxigenin, digoxigenin, or gitoxingenin. The calycin superfamily of proteins are characterized by structural motifs formed by anti-parallel, beta-sheets in a manner similar to the CDR region of immunoglobulins. Lipocalins, fatty acid-binding proteins ("FABPs") and avidins are members of the calycin superfamily of proteins. Calycins are relatively small secreted proteins that are believed to be involved in the binding and transport of hydrophobic molecules. The specificity of binding is determined by the conformation and constituent side-chains of the pocket created by folding of the protein. In vitro, many lipocalins can bind with high affinity to a range of hydrophobic molecules not normally encountered in nature. This may represent an inherent ability of the proteins to bind molecules having particular biochemical and structural properties. A calycin can be functionally divided into a "binding domain" and a "targeting domain." The "binding domain" functions to interact with ligands, while the "targeting domain" functions to provide specificity in transporting the bound ligand to a defined site. Known lipocalins include: retinol-binding protein; purpurin; retinoic acid-binding protein; alpha.sub.2u-globin; major urinary protein; bilin-binding protein; alpha-crustacyanin; pregnancy protein 14; beta.-lactoglobin; neutrophil lipocalin and choroid plexus protein; odorant-binding protein; von Ebner's gland protein; probasin; and aphrodisin. Lipocalins appear to have a regulatory influence on the inflammatory cascade and protect against excessive tissue damage. See, Flower D, *FEBS Letters* 354:7-11 (1994); Flower D, *J. Molec. Recognition* 8:185-195 (1995); Fowler D, *Biochem. J.* 318:1-14 (1996). Calycin proteins may be engineered to have a prescribed ligand specificity, as described in Schlehuber S and Skerra A, *Biophysical Chemistry* 96:213-228 (2002), U.S. Patent Application 20050106660 and PCT Applications WO 99/16873, WO 00/75308 (each of which applications is incorporated herein). As described in the foregoing PCT applications, the bilin-binding protein lipocalin has been specifically engineered to bind digoxigenin and therefore is included within the definition of digoxin antibody.

"digoxin binding capacity" means the amount of digoxin that is capable of being bound by a given amount of digoxin antibody. For example, a single vial of DIGIBIND® contains 38 mg total digoxin antibody and is capable of binding approximately 0.5 mg digoxin, i.e., one vial has 0.5 mg digoxin binding capacity. Thus, a vial having this formulation of DIGIBIND® has digoxin binding capacity of 0.013 mg digoxin or digitoxin bound per mg of antibody (0.5 mg digoxin÷38 mg total antibody). Similarly, a vial of the current formulation of DIGIFAB™ has 0.0125 mg digoxin or digitoxin bound per mg of antibody (0.5 mg÷40 mg total antibody).

"high dose" means an amount of a digoxin antibody composition having digoxin binding capacity that is greater than the digoxin binding capacity that would be used to treat the serum "digoxin" concentrations observed in pregnancy if the endogenous factors were, in fact, digoxin and if comparable digoxin concentrations were deemed to be poisonous or toxic so as to warrant treatment with digoxin antibodies. A high dose is an amount of digoxin antibody having digoxin binding capacity that is greater than the digoxin binding capacity in a single application dose for neutralizing digoxin/digitoxin toxicity in a subject having substantially the same serum digoxin/digitoxin concentration as the serum "digoxin" concentration observed in a pregnant woman. Preferably, when administered to treat a condition in which clinical symptoms of PIH or IUGR are present, a high dose comprises digoxin binding capacity of more than 0.006 mg per Kg patient weight; however, when administered to treat PIH or IUGR before manifestation of clinical symptoms (i.e., for prophylaxis), a high dose composition may also comprise digoxin binding capacity of ≦0.006 mg per Kg patient weight. More preferably, the digoxin binding capacity of a high dose digoxin antibody composition is between three-fold and one hundred-fold, and most preferably ten-fold, the digoxin binding capacity that would be used for treating digoxin/digitoxin intoxication in a patient having substantially the same serum digoxin/digitoxin concentration as the serum "digoxin" concentration observed in a pregnant woman. The high dose composition may be selected based upon either quantified serum "digoxin" or "digitoxin" concentration (such as by immunoassay) or based upon the amount believed to be present in the subject based upon the range of serum "digoxin" or "digitoxin" concentrations generally known to be present in pregnant patients, whether or not experiencing one or more symptoms of PIH or IUGR, and/or based upon the severity of PIH or IUGR symptoms or the risk factors (in kind or in number) for a patient to develop PIH or IUGR.

"antibody" or "antibodies" mean an immunoglobulin or any polypeptide or protein, whether natural or partly or wholly synthetically engineered or produced, having a binding domain which is, or is substantially homologous to, a binding domain for an antigen or an epitope of an antigen. Examples of antibodies are the immunoglobulin isotypes and their isotypic subclasses; antigen binding fragments; and diabodies (as defined below). The term also includes derivatives, functional equivalents and homologies of antibodies, including any polypeptide comprising a binding domain, whether natural or wholly or partially synthetic, polyclonal, monoclonal, humanized, chimeric or fully human. Various methods of producing such antibodies are described in U.S. Pat. No. 5,225,539, U.S. Pat. No. 5,693,761, U.S. Pat. No. 5,869,619, U.S. Pat. No. 5,821,337, U.S. Pat. No. 5,859,204, U.S. Pat. No. 6,946,546, U.S. Pat. No. 6,939,543, U.S. Pat. No. 6,926,896, U.S. Pat. No. 6,924,125, U.S. Pat. No. 6,893,624 and U.S. Pat. No. 6,881,557, each of which patents is incorporated herein by this reference.

"antigen binding fragments" or "binding fragments" mean fragments of whole antibodies and naturally occurring or synthetically constructed molecules that have a binding domain, whether specific or non-specific, for a ligand, an antigen or an epitope of an antigen.

"diabodies" mean multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form a binding domain. Binding domains are formed by the association of the first domain of one polypeptide within the multimer with the second domain of another polypeptide within the multimer (US Patent App. 2005/0214860, incorporated herein by this reference).

"binding domain" means the part of an antibody or of any other naturally occurring or synthetically engineered or constructed molecule, including, without limitation, a calycin protein, that binds to and/or is complementary to a part of or all of a ligand or an antigen or an epitope of an antigen. For purposes of the invention, an endogenous factor is deemed to be a ligand or an antigen.

"complementarity determining region" or "CDR" mean one or more of the three hypervariable sequences in the variable regions within each of the immunoglobulin light and heavy chains.

"mean arterial pressure" or "MAP" mean the pressure determined by either of the following formulae: [(2×diastolic pressure)+systolic pressure]÷3 OR diastolic pressure+⅓ (systolic pressure−diastolic pressure)

"S/D ratio" means, with respect to Doppler ultrasound, the ratio between the Doppler frequency shift during systolic flow and end diastolic flow in an artery or vein.

"RI" means, with respect to Doppler ultrasound, the resistance index of an artery or vein as determined by the formula (S−D)÷S, where "S" represents the Doppler frequency shift during systolic flow and "D" represents the Doppler frequency shift during end diastolic flow.

"creatinine clearance" or "CrCl" mean the test comparing the level of creatinine in urine with the creatinine level in the blood, usually based on measurements of a 24-hour urine sample and a blood sample drawn at the end of the 24-hour period. Clearance is often measured as milliliters/minute (mL/min). Creatinine clearance is used to estimate the glomerular filtration rate ("GFR"). The GFR, in turn, is the standard by which kidney function is determined. CrCl for women may be determined using the formula:

$$CrCl = (140 - age) \times (weight) \times 0.85 / (sCr \times 72)$$
("*sCr*"=serum creatinine concentration).

"mg" means milligram or milligrams.

"μg" or "mcg" means microgram or micrograms.

"ng" means nanogram or nanograms

"Kg" means kilogram or kilograms.

"mL" means milliliter or milliliters.

"Apgar" means the neonatal health assessment made after birth, preferably at the first and fifth minutes after birth, for each of: activity and muscle tone; pulse (heart rate); grimace (reflex irritability); appearance of skin coloration; and respiration (rate and effort). Each activity receives a score of 0 (lowest), 1 or 2 (highest). A total score of 7 or above, either on the first minute testing or as improved at the fifth minute testing, is generally considered to indicate good health.

"biophysical profile score" or "biophysical profile" or "BPS" mean the assessment of fetal wellness as determined by evaluation (biophysical profile procedure or "BPP") over a period of thirty minutes of (1) the non-stress test ("NST"), (2) ultrasound measurement of amniotic fluid volume ("AFV"), (3) presence/absence of fetal breathing movements, (4) gross body movements, and (5) tone. Each parameter receives a score of normal=2, abnormal=0 (for a maximum total score of 10 points). Alternatively, a modified BPP may initially evaluate only NST and AFV assessments and if either is abnormal then a complete BPP is performed.

| | | Risk of Fetal | | |
|---|---|---|---|---|
| Result | Interpretation | Risk (%) of Asphyxia* | Death (per 1000 per wk) | Recommended Treatment |
| 10/10 | Non-asphyxiated | 0 | 0.565 | Conservative |
| 8/10 normal AFV | Non-asphyxiated | 0 | 0.565 | Conservative |
| 8/8 w/o NST | Non-asphyxiated | 0 | 0.565 | Conservative |
| 8/10 ↓ AFV | Chronic compensated asphyxia | 5-10 | 20-30 | If ≧37 wk - deliver<br>If <37 wk - serial testing |
| 6/10 normal AFV | Acute asphyxia possible | 0 | 50 | If ≧37 wk - deliver<br>If <37 wk - repeat test w/in 24 hr. and if <6/10 - deliver |
| 6/10 ↓ AFV | Chronic asphyxia w/ possible acute | >10 | >50 | Factor in gestational age<br>If ≧32 wk - deliver<br>If <32 wk - test daily |
| 4/10 normal AFV | Acute asphyxia likely | 36 | 115 | Factor in gestational age<br>If ≧32 wk - deliver<br>If <32 wk - test daily |
| 4/10 ↓ AFV | Chronic asphyxia w/ acute asphyxia likely | >36 | >115 | If ≧26 wk - deliver |
| 2/10 normal AFV | Acute asphyxia almost certain | 73 | 220 | If ≧26 wk - deliver |
| 0/10 | Gross severe asphyxia | 100 | 100 | If ≧26 wk - deliver |

*Umbilical venous blood pH less than 7.25

"Clinical Global Impression" or "CGI" mean the clinical assessment of severity of a patient's condition at the time of evaluation ("CGI-S"), and the improvement in a patient's condition since a prior evaluation or initial severity screen ("CGI-I"). Maternal factors to assess CGI include, without limitation: physical examination, mental status, ECG, clinical laboratory results, vital signs, patient/family member reports, and medical professional reports. Fetal factors to assess for CGI include, without limitation: heart tracing, biophysical profile, and medical professional reports. The CGI is designed to document overall clinical impression of the patient's overall condition. The Clinical Global Impressions Scale described below has been modified from the scale presented by Guy by limiting the potential ratings to four for the Severity of Illness Scale and to three for the Improvement Scale. The original CGI-S scale is as follows: 1. Normal, not ill at all; 2. Borderline ill; 3. Mildly ill; 4. Moderately ill; 5. Markedly ill; 6. Severely ill; 7. Among the most extremely ill patients. The original CGI-I is as follows: 1. Very much improved; 2. Much improved; 3. Minimally improved; 4. No change; 5. Minimally worse; 6. Much worse; and 7. Very much worse. See, Guy W., ECDEU Assessment Manual for Psychopharmacology—Revised, Rockville, Md., U.S. Dept. Health and Human Services [Publ No ADM 76-338] (1976, pgs. 218-222). Although the CGI-S and CGI-I scales described below are preferred, for purposes of the invention the original Guy scales or any modified form of a CGI-S and/or CGI-I scale may be used.

| Severity Scale (CGI-S) | Improvement (or Change) Scale (CGI-I) |
|---|---|
| 1. Normal, not ill at all. | 1. Improved. |
| 2. Mildly ill. | 2. No change. |
| 3. Moderately ill. | 3. Worse. |
| 4. Severely ill. | |

II. Etiology of PIH and IUGR

In the early stages of pregnancy, the placenta has a "loose" connection with the uterine wall. Around the fourteenth to sixteenth week of normal pregnancy, the placenta develops a "tight" attachment to the uterine wall in order to tap more fully into the maternal blood supply. During this normal placental development, trophoblasts invade the maternal spiral arterioles and completely remodel the maternal spiral arterioles into large capacitance vessels with low resistance, allowing for the exchange of larger and more complex nutrients that are required for the continued development of the fetus at the later stages of the pregnancy. Furthermore, during normal differentiation, in a process known as pseudovasculogenesis, invasive trophoblasts alter their adhesion molecule expression from those characteristic of epithelial cells (integrin $\alpha_6/\beta_3$ and $\alpha\omega/\beta_5$, and E-cadherein) to those of endothelial cells (integrin $\alpha_1/\beta_1$ and $\alpha\omega/\beta_3$, platelet endothelial cell adhesion molecule and vascular endothelial-cadherin). In preeclampsia, shallow placental trophoblast invasion of the uterine spiral arterioles leads to reduced placental perfusion and placental insufficiency.

PIH is known to cause vasoconstriction and vasospasm, damaging the smooth muscle lining of the blood vessels. This damage to blood vessels can also lead to edema, including cerebral edema. Vasospasm can occur throughout the body, damaging the heart, kidneys, liver and brain. Vascular damage leads to the accumulation of platelets in the blood vessels, forming small clots along the blood vessel wall and further narrowing the blood vessel, resulting in further vasoconstriction. This cascade of events exacerbates the severity of the maternal hypertensive condition and increases the risk for developing or the severity of IUGR.

The fetus is connected by the umbilical cord to the placenta and receives nutrition and oxygenation from the maternal circulation through the placenta. Oxygenated blood travels from the placenta through the umbilical vein to the fetal heart, where it then is distributed to fetal tissues and is finally returned (along with metabolic wastes) to the placenta through two umbilical arteries. In PIH, hypertension, vasoconstriction, vasospasm and exaggerated myocardial function may, individually or together, negatively impact the flow of blood to the placenta, and consequently to the fetus, such that little or no blood flows to the placenta and fetus (i.e., there is insufficient placental and fetal perfusion).

Figure 2:
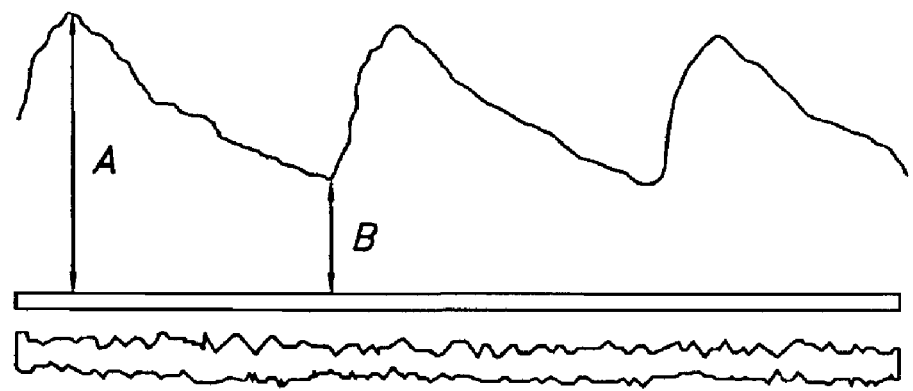
FIG. 2 is a diagram illustrating Doppler ultrasound wave shifts in an umbilical artery of a normotensive patient.
Figure 3:
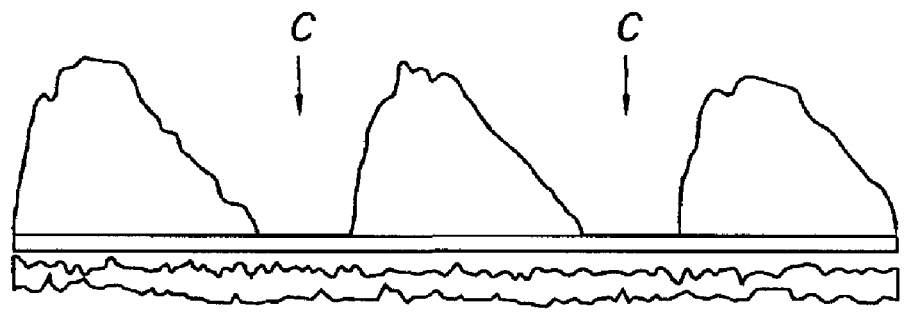
FIG. 3 is a diagram illustrating Doppler ultrasound wave shifts in an umbilical artery of a preeclamptic patient.

FIG. 2 illustrates the blood flow velocity in the umbilical artery of a normal pregnancy. In FIG. 2, "A" refers to the blood flow velocity during systole, while "B" refers to the blood flow velocity in the umbilical artery during end diastole. FIG. 2 illustrates that in a normal pregnancy, even during diastole, there is a significant flow velocity through the umbilical artery. This is in contrast to the flow velocity in a preeclamptic patient, as illustrated in FIG. 3. In PIH, reduced fetal perfusion is evidenced by umbilical artery flow velocity "bottoming out" (being reduced or absent) during diastole, indicated in FIG. 3 by "C". In the most severe circumstance, the direction of umbilical artery flow may become reversed. Maternal vasoconstriction results in restricted blood flow to and through the fetus and reduced flow (and disposal of metabolic wastes) from the fetus through the umbilical artery back to the maternal circulation. Reduced placental and fetal perfusion results in reduced oxygenation and fluid exchange (nutrition and waste removal) and may cause or contribute to IUGR.

The reduced placental perfusion makes the exchange of nutrients and metabolic waste removal through the placenta more difficult. It is known that many nutrient transport processes across the placenta (specifically across the microvillus membrane of syncytiotrophoblasts) are sodium-coupled and are dependent upon the maintenance of a low intracellular $Na^+$ concentration. It is also known that sodium/potassium ATPase activity is reduced in the microvillus membrane of syncytiotrophoblasts isolated from the placentas of IUGR pregnancies. Applicant theorizes that inhibition of sodium/potassium ATPase may cause or contribute to IUGR because of the reduced ability of the placenta and fetus to receive nutrients and dispose of metabolic wastes necessary for continued fetal growth and development.

III. Endogenous Sodium Pump Inhibitors in PIH and IUGR

A. Endogenous Factors Associated with PIH and IUGR.

It is theorized by Applicant that the failure of the placenta to properly invade the uterine wall is associated with the release of abnormal levels of endogenous factors from placental, fetal and/or maternal sources. Endogenous sodium pump inhibitors are found in patients having mineralocorticoid hypertension (primary aldosteronism and ectopic corticotrophin syndrome), essential hypertension and hypertension in plasma-volume expanded states, including normotensive pregnancy and pregnancy complicated by PIH. It is known that these endogenous factors inhibit $Na^+/K^+$ ATPase activity in vitro. Applicant has discovered that, in vivo, red blood cells of preeclamptic patients exhibit decreased sodium pump activity and that this sodium pump inhibition is reduced or reversed by administration of high dose digoxin antibody compositions to the preeclamptic patient. Thus, it has been discovered by Applicant that these endogenous factors cause or contribute to one or more symptoms or complications of PIH or IUGR.

These endogenous factors have not been fully characterized but have been generally referred to as digitalis-like or digoxin-like because they have physical, chemical and biological characteristics similar to those of cardenolides and bufadienolides, which are known cardiotonic steroids. The endogenous factors have been variously described as "endoxin," "endobain," "digoxin-like," "digitalis-like," dihydrodigoxin, "endogenous ouabain," "ouabain-like," dihyrooubain, "proscillaridin A-like," "endogenous marinobufagenin," "marinobufagenin-like," "bufalin-like" and 19-norbufalin. Digitalis-like, ouabain-like, bufalin-like and marinobufagenin-like endogenous factors have been specifically observed in neonates, normotensive pregnancy and in PIH.

It is believed by Applicant that these EFs may inhibit sodium pump activity through direct or indirect binding of one or more isoforms of the sodium pump or of other membrane-bound proteins that influence sodium pump activity, or through regulation of sodium pump expression, degradation or recycling, or through some other regulatory mechanism directly or indirectly affecting the sodium pump.

B. Cardiac Glycosides—Exogenous Sodium Pump Inhibitors.

Figure 5A:
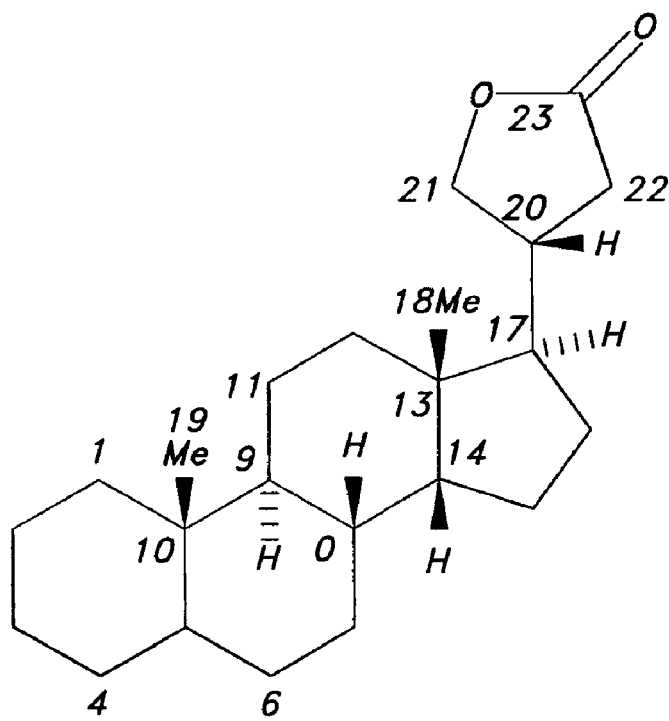
FIG. 5a is an example of the aglycone structure of a cardenolide.
Figure 5B:
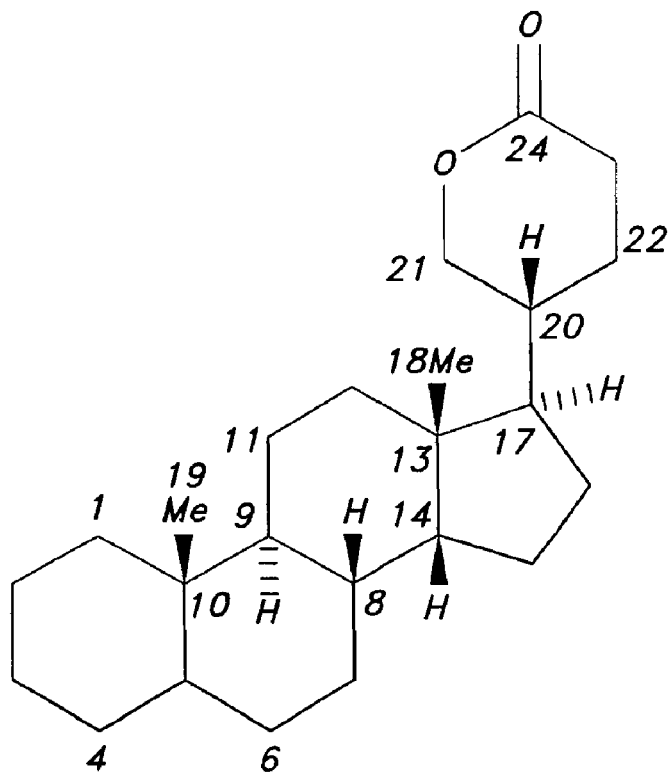
FIG. 5b is an example of the aglycone structure of a bufadienolide.

Cardiac glycosides are composed of two structural features, the sugar (glycoside) and the non-sugar (aglycone) steroid moieties. The glycoside moiety may not significantly affect sodium pump binding affinity but may alter the biopharmaceutical or pharmacokinetic properties of the cardiac glycoside. See, Pullen, M. A., et al., *J. Pharm. Exp. Therapeutics* 310(10): 319-325 (2004). Aglycones of the general class of cardenolides and bufadienolides are shown, respectively, in FIGS. 5a and 5b.

Cardenolides and bufadienolides are known to specifically inhibit $Na^+/K^+$ ATPase. The sodium pump is responsible for establishing and maintaining the electrochemical gradient of sodium and potassium ions across the plasma membrane of mammalian cells, maintaining the intracellular cytoplasm high in $K^+$ and low in $Na^+$. The presence of a binding site for exogenous sodium pump inhibitors suggests that one or more endogenous "digoxin-like" factors may be involved in the regulation of sodium homeostasis, blood pressure and volume.

C. Antibodies to Cardiac Glycosides as Therapeutic Agents.

Digitalis or its constituents, digoxin and digitoxin, are the primary cardiotonic steroids that are used therapeutically to treat cardiac arrhythmias and congestive heart failure. Digoxin and digitoxin have a narrow therapeutic range (1.0-1.9 nmol/L or approximately 0.8-1.5 ng/mL serum digoxin concentration) and overdose to these drugs is not uncommon. Digoxin overdose and life-threatening digoxin toxicity are treated through the administration of antibodies to digoxin. It is believed that antibodies counteract the effects of digoxin or digitalis because the binding domain of the antibody binds to the cardiac glycoside thereby preventing it from binding to or otherwise inhibiting or regulating the expression or function of $Na^+/K^+$ ATPase. If the antibodies are specific to the cardiac glycoside they will bind it with high affinity, favoring movement of the cardiac glycoside out of tissue and allowing the resulting antigen/antibody complex to be eliminated from the body. Reversal of $Na^+/K^+$ ATPase inhibition caused by cardiac glycosides is believed to be due to the greater affinity of the antibodies for the cardenolide or bufadienolide, than the affinity of the cardenolide or bufadienolide for $Na^+/K^+$ ATPase.

D. Role of Endogenous Sodium Pump Inhibitors in PIH and IUGR.

Applicant has theorized that elevated levels of EFs in PIH and IUGR inhibit the normal functioning of, or regulate at least some isoforms or subunits of, $Na^+/K^+$ ATPase, causing intracellular levels of sodium and calcium ions to rise. When normal vascular endothelial cell osmolality is altered, an influx of water may rupture the endothelial cells causing an inflammatory response that further constricts the interior diameter of the vasculature, thereby contributing to the hypertensive state. Vasoconstriction may produce exaggerated myocardial function due to the increased effort required by the heart to pump blood through the narrowed vasculature. It is also possible that exaggerated myocardial function results from direct action of the endogenous factor(s) on cardiac muscle cells. Vascular responsiveness to vasoactive agents may also be affected by deviations from the normal balance of sodium, potassium and calcium ions within the vascular endothelia. It is believed by Applicant that this intracellular ion imbalance within cells of the placenta, vasculature, brain and/or kidneys leads to, inter alia, intravascular volume contraction, vasoconstriction, vasospasm and may lead to or contribute to IUGR. Furthermore, alteration in the capacity of the syncytiotrophoblast $Na^+/K^+$ ATPase to maintain the $Na^+$ gradient may indirectly affect the sodium-dependent or sodium-coupled transport systems of the placenta (such as amino acid and phosphate uptake), impairing nutrient and oxygen supply and extrusion of protons ($H^+$) from the syncytiotrophoblasts, resulting in or contributing to IUGR.

It is known that in vitro sodium pump inhibition by EFs may be reversed or prevented by addition of antibodies to cardenolides and bufadienolides, particularly anti-digoxin antibodies. Pullen, M. A, et al., *J Pharm. Exp. Therapeutics* 310:319-325 (2004). Applicant has discovered that in vivo administration of a high dose digoxin antibody composition also reduces or reverses sodium pump inhibition or otherwise increases sodium pump activity. Thus, it is believed that antibodies to cardenolides and bufadienolides may be useful in diagnosing, preventing and/or treating PIH.

VI. Therapeutic Antibodies in General

Passive immunity is conferred when antibodies generated in one source are administered to a different source in order to prevent or treat a disease or an infection, or to neutralize toxicity. Applicant has discovered that antibodies used to treat cardiotonic steroid intoxication in humans are also effective for treating the causes or symptoms of PIH and IUGR. Applicant believes that these antibodies bind to EFs such that the antibody-EFs complex may be removed from the body, effectively treating or controlling one or more of the causes or the symptoms or complications of PIH and IUGR. If symptoms or complications or causes of PIH or IUGR may be treated or controlled, ultimately the pregnancy may be continued, premature delivery may be delayed or avoided, fetal development may continue and the maternal and fetal conditions and outcomes may be improved.

A. Introduction to the Immune System.

Blood is comprised of a variety of cells, including platelets, red blood cells and leucocytes (monocytes, neutrophils, eosinophils, mast cells, basophils) and circulating lymphocytes (B-cells and T-cells). Each leucocyte and lymphocyte has a different responsibility, but all function together for the primary objective of recognizing, attacking and destroying bacteria, viruses, cancer cells, and all substances seen as foreign.

The major function of B lymphocytes is the production of antibodies in response to foreign substances, including bacteria, viruses, and tumor cells. Antibodies are specialized proteins that specifically recognize and bind to one particular molecule or protein. Each B lymphocyte expresses a surface antibody having a unique binding domain for one antigen. When an antigen is large, an antibody may only bind to a particular part of the antigen, which part is referred to as an epitope. Antibody binding is generally specific for one antigen or an epitope of an antigen, and the antigen-antibody binding is usually of high affinity.

The unique binding domains of antibodies are not the result of exposure to the antigen, but arise through random genetic rearrangements. When a B-cell encounters an antigen, the B-cell is activated to differentiate into a plasma cell, secreting different classes of antibodies (such as IgG, IgA or IgM) having the same binding domain. Antigen recognition and binding allows antibodies to initiate the complement system, a complex biochemical cascade of more than 35 serum protein that leads to, inter alia, opsonization and cytolysis of antigen presenting cells (foreign cells or macrophages/neutrophils that have small portions of digested antigens on the exterior surface of their cell membranes).

Opsonization is a process through which bacteria, virus-infected cells and other cells are targeted for destruction. Antibodies serve as "tags" (opsonins) because one end (the Fab) binds to an antigen on the foreign cell while the other end of the antibody (the Fc) binds to receptors on phagocytic cells (e.g., macrophages and neutrophils). The antibody-antigen complex signals the phagocyte to engulf and destroy the antigenic organism or cell. Activation of the complement system also causes formation of an aggregate of complement proteins (Membrane Attack Complex or "MAC"). MAC is capable of inserting itself into the cell membrane of an antigen presenting cell, creating holes that allow ions, water and other small molecules to freely pass through the membrane (the MAC attack). As a result, the antigen presenting cell will not be able to maintain its osmolality and will quickly die or undergo cytolysis.

B. Antibodies in General.

All naturally occurring whole antibodies have a common core structure of two identical light chains, each being about 24 kilodaltons, and two identical heavy chains each being about 55-70 kilodaltons. One light chain is attached to each heavy chain, and the two heavy chains are attached to each other. Both the light and heavy chains contain a series of repeating homologous units, each of about 110 amino acid residues in length which fold independently in a common motif called an immunoglobulin (Ig) domain. All Ig domains contain the complementarity determining regions ("CDR"), which are specific for and bind to the antigen or epitope. There are between $10^8$ and $10^{10}$ structurally different antibody molecules in every individual. Antibody sequence diversity is predominantly found in three short amino acid sequences within the amino terminal variable domains of the heavy and light chains, called the hypervariable regions, to distinguish them from the more conserved "framework regions" that flank each CDR within the variable regions of the light and heavy chains.

Despite their overall similarity, antibody molecules can be divided into distinct classes and subclasses based on physio-chemical characteristics such as size, charge and solubility, and on their behavior in binding to antigens. In humans, the classes of antibody molecules include IgA, IgD, IgE, IgG and IgM. Members of each class are said to be of the same isotype. IgA and IgG isotypes are further subdivided into subtypes called IgA.sub.1, IgA.sub.2 and IgG.sub.1, IgG.sub.2, IgG.sub.3 and IgG.sub.4. The heavy chains of all antibody molecules in an isotype share extensive regions of amino acid sequence identity, but differ from antibodies belonging to other isotypes or subtypes. Heavy chains are designated to the overall isotype of the antibody molecule, e.g., IgA contains "alpha", IgD contains "delta", IgE contains "epsilon", IgG contains "gamma", and IgM contains "mu". IgG, IgE and IgD circulate as monomers. IgA circulates as a monomer, and molecules secreted through the epithelia into the mucosal lining of body cavities are homodimers. IgM molecules form pentamers.

C. Production of Antibodies.

Animals may be inoculated with an antigen in order to produce antibodies specific for the antigen. Frequently an antigen is bound or conjugated to another molecule to enhance the immune response. As used herein, a conjugate is any peptide, polypeptide, protein or non-proteinaceous compound bound to an antigen that is used to elicit an immune response. Antibodies produced in an animal in response to antigen inoculation comprise a variety of non-identical molecules (polyclonal antibodies) made from a variety of individual antibody producing B lymphocytes. The epitope is the specific antigenic structure recognized by the binding domain. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope on the antigen because all antibody producing cells are derived from a single B-lymphocyte cell line. Hybridoma technology involves the fusion of a single B lymphocyte with an immortal myeloma cell (usually mouse myeloma). This technology provides a method to propagate a single antibody-producing cell for an indefinite number of generations, such that unlimited quantities of structurally identical antibodies having the same antigen specificity (monoclonal antibodies) may be produced. However, in therapeutic applications a goal of hybridoma technology is to reduce the immune reaction in humans that may result from administration of monoclonal antibodies generated by the non-human (e.g. mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences.

It is thought that replacement of amino acid sequences in the antibody that are characteristic of rodents with amino acid sequences found in the corresponding position of human antibodies will reduce the likelihood of immune reaction during therapeutic use. A hybridoma or other cell producing an antibody may also be subject to genetic mutation or other changes, which may or may not alter the binding specificity of antibodies produced by the hybridoma.

It is possible to take monoclonal and other antibodies and use recombinant DNA technology to produce other antibodies or chimeric molecules which retain the antigen specificity of the original antibody, i.e., the molecule has a binding domain. Such techniques may involve introducing DNA encoding the immunoglobulin variable region or the CDRs of an antibody to the framework regions, constant regions, or constant regions plus framework regions, of a different antibody. See, for instance, U.S. Pat. No. 5,091,513, and U.S. Pat. No. 6,881,557 which are incorporated herein by this reference.

These antigen binding fragments have binding specificity (binding domain) for the antigen, but lack amino acid sequences in the conserved framework region, so they are less likely to elicit an immune response in a patient. An antigen binding fragment preferably has a binding domain provided by one or more antibody variable domains and, most preferably, a binding domain of an antibody comprises an antibody light chain variable region (VL) and an antibody heavy chain variable region (VH).

Examples of antigen binding fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) "diabodies", multivalent or multispecific fragments constructed by gene fusion (US 2005/0214860). Fv, scFv or diabody molecules may be stabilized by the incorporation of disulphide bridges linking the VH and VL domains. Minibodies comprising a scFv joined to a CH3 domain may also be made (S. Hu et al, *Cancer Res.*, 56, 3055-3061, (1996)).

By known means as described above, polyclonal or monoclonal antibodies (humanized, fully human or chimeric), antigen binding fragments and binding domains may be created that are specific to cardenolides and bufadienolides, their aglycone moieties, or conjugates of any of the foregoing, whether such antigens are isolated from natural sources or are synthetic derivatives or variants of the natural compounds.

Antibodies may be produced from any animal origin, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546 which is incorporated herein by this reference. Theses techniques are further described in: Marks, *Bio/Technology* 10:779-783 (1992); Stemmer, *Nature* 370:389-391 (1994); Gram et al., *Proc. Natl. Acad. Sci., USA*, 89:3576-3580 (1992); Barbas et al., *Proc. Natl. Acad. Sci., USA*, 91:3809-3813 (1994); and Schier et al., *J. Mol. Biol.* 263:551-567 (1996).

Methods for producing polyclonal antibodies in various animal species as well as for producing monoclonal antibodies of various types, including humanized, chimeric, and fully human, are well known in the art and highly predictable. In addition, antibodies to various cardiac glycosides, including digoxin, ouabain, bufalin and marinobufagenin, are commercially available, and methods for producing these antibodies are also well known and predictable. For example, the following U.S. patents and patent applications provide enabling descriptions of such methods and are herein incorporated by reference: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003;

4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. In addition, all patents, patent application publications, and other publications cited herein and therein are hereby incorporated by reference in the present application.

It is fully expected that antibodies to a specific cardenolide or bufadienolide will have the ability to neutralize or counteract the effects of the cardiac glycoside regardless of the animal species, monoclonal cell line or other source of the antibody. For example, although the antibody used in the Biological Examples of the present application was produced in sheep, it is expected that other animals immunized with the same or a similar cardenolide or bufadienolide would yield polyclonal antibodies effective for the purposes of the present invention. Certain animal species may be less preferable for generating therapeutic antibodies because they may cause an increased likelihood of allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will illicit an undesirable immunological response, and, thus, antibodies without Fc may be preferential for prophylactic or therapeutic treatments. As described above, antibodies may also be constructed so as to be chimeric, partially or fully human, so as to reduce or eliminate the immunological consequences resulting from administering to an animal an antibody that has been produced in, or has sequences from, another species.

Furthermore, it is known that antibodies to a specific cardenolide or bufadienolide will cross-react with other cardenolides and bufadienolides, although in a less specific manner. Thus, it is believed that a cross-reactive antibody will have the ability to neutralize or counteract the effect of the non-specific cardiac glycoside. For example, anti-marinobufagenin antibody is known to have cross-reactivity (expressed as a percentage) to various cardiotonic steroids as follows: marinobufagenin (100%); ouabain (0.1%); digoxin (1.0%); digitoxin (3.0%); bufalin (1.0%); proscillaridin (1.0%). Anti-ouabain antibody is known to have cross-reactivity to various cardiotonic steroids as follows: ouabain (100%); digitoxin (7.4%); proscillaridin (0.2%); marinobufagenin (0.5%); bufalin (0.03%). Anti-digoxin antibody is known to have cross-reactivity to various cardiotonic steroids as follows: digoxin (100%); ouabain (0.4%); oubagenin (0.1%); marinobufagenin (0.2%); bufalin (2.7%); cinobufotalin (4.3%); cinobufagin (0.02%). These examples of immunological cross-reactivity are not intended to limit in any manner the scope of the inventions disclosed herein.

If the non-specific binding results in diminished antigen-antibody affinity or if the cardenolide or bufadienolide has biopharmaceutical or pharmacokinetic characteristics that differ from the cardiac glycoside that is specific for the antibody, then a greater amount of antibody may be required to neutralize or counteract the effects of the non-specific cardenolide or bufadienolide. Nevertheless, it is fully expected and is known that in vitro antibodies to a specific cardenolide or bufadienolide will have the ability to counteract the sodium pump inhibition caused by a different cardenolide or bufadienolide. One may design appropriate antibody compositions and dosing regimens by taking into account the level of sodium pump inhibition, the cross-reactivity, binding affinity or avidity, biopharmaceutical and/or pharmacokinetic properties of the specific as compared to the non-specific cardenolide or bufadienolide.

D. Passive Immunity—Neutralizing Antibody Dose Determination.

Determination of an effective antibody composition to neutralize intoxication by an exogenous antigen usually requires, inter alia, a determination of the body load of antigen that must be bound or neutralized by the antibody. Factors that influence effective antibody compositions include, inter alia, known or suspected total body load of antigen, whether it has reached steady-state equilibrium, bioavailability (free and protein bound), biopharmaceutic and pharmacokinetics of the antigen (e.g. antigen affinity for its receptor and bioactivity), patient weight or volume, history and renal function. Generally, when an antigen reaches equilibrium within the body, antigen concentration (bound and unbound) in tissues and in extracellular fluids is reflected by the plasma or serum concentration. Total body load of the exogenous antigen generally equals the steady-state serum concentration of the antigen multiplied by the apparent volume of distribution (the fluid volume required to contain the antigen in the body at the same concentration as in plasma). Thus, the antibody composition generally required to neutralize the total body load may be determined from the amount of antigen bound by a single unit of antibody, which is referred to herein as the binding capacity of the unit, multiplied by the total body load of the antigen.

E. Endogenous Factors React with Antibodies to Cardiac Glycosides.

Endogenous factors are known to be immunoreactive to antibodies against a number of exogenous cardiac glycosides. The body load of an exogenous antigen, which is necessary to determine an effective neutralizing antibody composition, may be determined by immunoassay for the antigen. However, there is no known commercially available antibody or immunoassay specific for endogenous "digoxin-like" factors. Commercially available immunoassays have been developed to detect digoxin, ouabain, bufalin and marinobufagenin. These commercially available immunoassays have been used to detect serum levels of "digoxin," "ouabain," "bufalin" or "marinobufagenin" in preeclamptic patients that have never been given or exposed to any of these exogenous cardenolides or bufadienolides. These levels have previously been believed to accurately represent the level of EFs in these patients.

Applicant believes that immunoassays specific for exogenous cardenolides or bufadienolides, including digoxin immunoassays, have not accurately detected levels of EFs present in humans. It is known that cross-reactivity of EFs to cardiac glycoside antibodies does not always correlate with the ability of the EFs to cause sodium pump inhibition. Sodium pump inhibition by EFs is often greater than would be expected based upon serum levels of EFs (e.g., "digoxin" or "ouabain-like compound," "bufalin" or "marinobufagenin") detected by immunoassay. Also, it is theorized that a substantial portion of EFs, perhaps up to 90%, are protein-bound and not detectable by direct measurement with conventional immunoassays. Pullen, M. A., et al., *J. Pharm. Exp. Therapeutics* 310(10): 319-325 (2004); Valdes, R. and Graves, S. W., Protein binding of Endogenous Digoxin-immunoactive Factors in Human Serum and its Variation with Clinical Condition, *J. Clin. Endocrinol. Metabol.* 60:1135-1143 (1985).

Furthermore, because EFs are likely to be continuously generated in the mammal, the total body load of EFs may not necessarily be determined by the manner used to determine total body load (steady state equilibrium) of an exogenous antigen. In mammals, EFs may not reach "steady state" or "steady state" may be in constant flux. Thus, serum concentrations of endogenous factors detected by immunoassay for "digoxin", "ouabain", "bufalin" or "marinobufagenin" are not likely to accurately measure the total body load of EFs at a given time. Thus, it is likely that levels of endogenous factors detected by known immunoassays represent only a portion of bioactive endogenous factors present in the maternal/fetal circulation. It is also possible that more than one form or type of endogenous factor is present in PIH and IUGR and that immunoassays for these exogenous cardiotonic steroids have not detected certain types of EFs.

The discrepancy in immunoassay measurements of EFs and the discordance between cardiac glycoside immunoactivity and sodium pump inhibition suggest that endogenous factors are not digoxin, ouabain, bufalin or marinobufagenin, but one or more compounds that differ in biological, chemical, physical, biopharmaceutical and/or pharmacokinetic characteristics from these exogenous cardiac glycosides. Miyagi, H. et al, Ouabain-like Na/K-ATPase Inhibitory Activity of a Plasma Extract in Normal Pregnancy and Pregnancy Induced Hypertension, *Japan. J. Pharmacol.* 57: 571-581 (1991).

If antibodies to cardenolides and bufadienolides are to be useful in diagnosing or treating the causes or symptoms of PIH and IUGR, conventional antibody compositions to neutralize cardiac glycoside intoxication (e.g., based upon measurements of EFs from immunoassays for exogenous cardiac glycosides, including digoxin, ouabain, bufalin or marinobufagenin) are not likely to be accurate or effective. Applicant has surprisingly discovered that digoxin antibody compositions having high doses of digoxin binding capacity are effective to treat the causes, symptoms and complications of PIH and IUGR.

VII. Therapeutic Antibody Treatment of PIH and IUGR

It is proposed that digoxin antibodies may be given to a patient in a therapeutically effective amount to treat one or more of the causes, symptoms or complications of PIH or IUGR, according to the flow diagram of FIG. 1. Similarly, if prior to onset of symptoms a patient is determined to have a propensity for or to be at risk for developing PIH or IUGR, a therapeutically effective amount of digoxin antibody may be administered for prophylaxis. It should be emphasized, however, that the present invention is not limited to any particular composition, dosage or range of dosages of digoxin antibodies, or antibodies from any particular source.

A therapeutically effective digoxin antibody composition, when administered to a patient exhibiting symptoms or complications of PIH or IUGR, will preferably provide a clinically beneficial effect, and most preferably a statistically significant effect, namely the alleviation, amelioration, reduction or inhibition of or improvement in one or more symptoms or complications of PIH or IUGR, or improvement in the patient's general condition. A clinically beneficial effect results in a beneficial change from baseline (i.e., before administration of digoxin antibody) for a specific medical parameter. Preferably, a clinical beneficial effect results in a reduction in CGI-S or a positive change in CGI-I for the patient. Alternatively, a clinically beneficial effect results in a systolic blood pressure of 140 or less, a diastolic blood pressure of 90 or less, or a mean arterial pressure of 106 or less. A statistically significant effect results in a change in a parameter from baseline that results in a statistical significance such that "P" is less than or equal to 0.05, whether statistical significance is determined with respect to changes in an individual patient or within a population of patients. Alternatively, a therapeutically effective amount is an amount sufficient to stabilize a symptom of PIH or IUGR such that the symptom does not materially worsen.

Figure 4A:
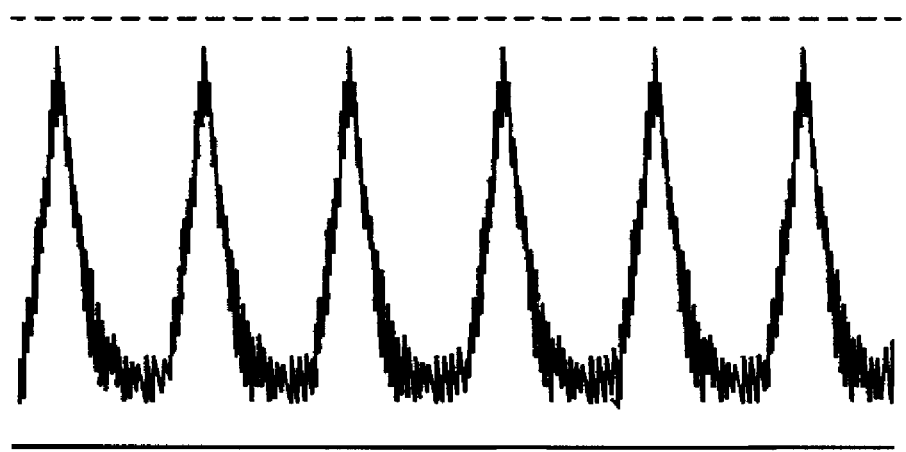
FIG. 4a is a Doppler ultrasound chart illustrating blood flow velocity through a preeclamptic patient's umbilical artery before administration of a high dose digoxin antibody composition.
Figure 4B:
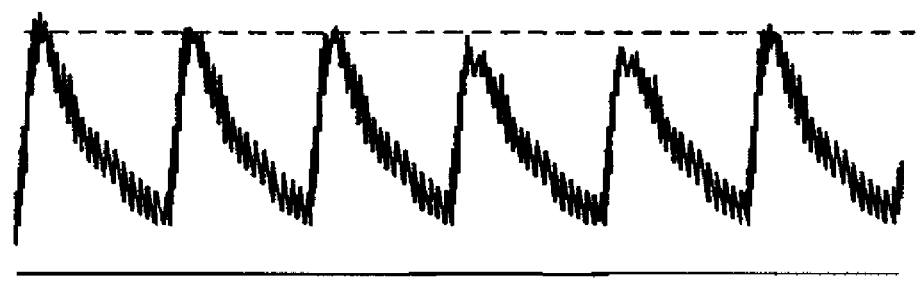
FIG. 4b is a Doppler ultrasound chart illustrating blood flow velocity through a preeclamptic patient's umbilical artery after administration of a high dose digoxin antibody composition.

A therapeutically effective digoxin antibody composition may also provide increased placental and fetal perfusion and/or increased middle cerebral artery (fetal or maternal), umbilical artery or umbilical venous flow or reduced constriction. Alternatively, as shown in FIG. 4b, a therapeutically effective composition provides improvement in middle cerebral artery (fetal or maternal), umbilical artery or umbilical vein systolic or diastolic blood pressures or systolic/diastolic ratio ("S/D ratio"), or improvement in the resistance index ("RI") of the middle cerebral artery (fetal or maternal), umbilical artery or umbilical vein.

A therapeutically effective digoxin antibody composition may also increase $Na^+/K^+$ ATPase function and/or $Na^+/K^+$ facilitated nutrient transport in one or more cell types or tissues, preferably in trophoblasts, syncytiotrophoblasts, other placental and fetal cells, vascular endothelial cells, red blood cells, leucocytes, lymphocytes and renal cells. A therapeutically effective amount may also be the amount necessary to increase $Na^+/K^+$ ATPase gene expression (e.g. increases in messenger ribonucleic acid (mRNA) corresponding to a sodium pump gene, which mRNAs are transcribed into polypeptides or proteins that form the sodium pump), or to decrease $Na^+/K^+$ ATPase degradation or recycling in particular cells or tissues affected by endogenous factors, particularly vascular endothelial cells, red blood cells, leucocytes, lymphocytes, renal cells, cardiac cells, neural cells, trophoblasts, syncytiotrophoblasts, other placental cells and fetal cells.

Parameters that may be evaluated for or that may indicate therapeutic efficacy of a digoxin antibody composition may include, without limitation: GCI-S or GCI-I; systolic or diastolic blood pressure, or mean arterial pressure; urinary output, urinary protein levels (proteinuria) or creatinine clearance; middle cerebral artery (fetal or maternal) or umbilical artery or umbilical venous flow, S/D ratio or RI; serum creatinine, LDH, liver enzymes, bilirubin or BUN levels; platelet count or hemolysis; fetal development (estimated weight for gestational age and maternal abdominal circumference for gestational age) or fetal biophysical profile score; peripheral edema, pulmonary edema, cerebral edema and cerebral hemorrhage (including fetal periventricular and intraventricular hemorrhage); scotomata, double or blurred vision, amaurosis, cortical blindness, retinal detachment; and neurological function and/or neurological responsiveness, consciousness, mental status or neurological disturbances (e.g., seizure, hyper reflexia, central nervous system irritability, clonus).

In all methods of the invention, therapeutically effective digoxin antibody compositions may be readily determined by one of ordinary skill in the art by monitoring the patient for signs of absence, stabilization, amelioration, reduction, inhibition, or improvement in one or more indications, symptoms or complications of PIH or IUGR (e.g., the parameters described in the preceding paragraph), and correspondingly maintaining, increasing or decreasing the amount of digoxin antibody and/or frequency or manner of administration, as determined by clinical judgment.

The composition of the digoxin antibody administered to achieve the desired therapeutic effect may depend upon a number of factors, for example, the mode of administration, the recipient's physical condition (including presence of any disease, symptom or syndrome), gestational age or the anticipated duration of antibody treatment, the existence of predisposing factors for any disease, symptom or syndrome (particularly risk factors for PIH or IUGR), the severity of the condition or symptoms being treated, the patient response to one or more previously administered doses of the antibody and patient response to other drugs or compositions being administered.

The compositions of the invention may be administered to a mammal by any, or a combination of several, means, including, without limitation, oral, intravenous, transmucosal (e.g. nasal, vaginal, etc.), pulmonary, subcutaneous or intradermal or transdermal (injection or infusion or patch), ocular, buccal, sublingual, intraperitoneal, intrathecal, intramuscular or long term depot preparation. For subcutaneous, intradermal, transdermal, intramuscular or intravenous administration (including intravenous bolus injections or bolus infusions), the composition may contain physiologically acceptable solutes, diluents or excipients including, without limitation, glucose, dextrose, saline, Ringer's or lactated Ringer's solution, Sterile Water for Injection, water or other suitable excipients. For intravenous administration, a loading dose may be administered by intravenous bolus injection or bolus infusion to achieve a target concentration and may then be followed by a sustained intravenous infusion of one or more compositions.

Antibodies to various cardenolides and bufadienolides are well known in the art, including, without limitation, antibodies to digoxin, ouabain and marinobufagenin. Because digoxin and digitoxin are the primary cardiotonic steroids that are used as therapeutic agents, anti-digoxin antibody products have been developed to treat digoxin or digitoxin overdose, are well known in the art and have been specifically approved for therapeutic use in connection with potentially life-threatening digoxin and digitoxin intoxication. In rare instances, antibodies against digoxin or digitoxin (or conjugates thereof) have also been used "off label" to treat life-threatening intoxication by other exogenous cardenolides or bufadienolides. *Morbidity and Mortality Weekly Report* 44(46):853-855, 861 (Nov. 24, 1995) (treatment was effective in some, but not all, patients); Eddleston, M. and Warrell, D. A., Management of Acute Yellow Oleander Poisoning, *Q J Med.* 92:483-485 (1999) (treatment was effective in some, but not all, patients). See, also, Brubacher J R, Ravikumar P R, Bania T, Heller M B, Hoffman R S, *Chest* 110:1282-1288 (1996); Brubacher J R, Lachmanen D, Ravikumar P R, Hoffman R S, *Toxicon* 37:931-942 (1999).

Digoxin immune Fab (ovine) compositions effective for treating life-threatening digoxin/digitoxin intoxication are currently marketed by GlaxoSmithKline in the United States under the brand name DIGIBIND® and by Protherics, Inc. under the brand name DIGIFAB™. Digoxin immune Fab products effective for treating life-threatening digoxin/digitoxin intoxication are produced and marketed outside the United States under other brand names. See Clinical studies comparing DIGIBIND® and DIGIFAB™ indicate that these products have equivalent pharmacokinetics and the proportion of patients responding to DIGIFAB™ were similar to, and consistent with, the historical data available for DIGIBIND®.

DIGIBIND® is a sterile lyophilized powder of antigen binding fragments (Fab) derived from specific antidigoxin antibodies raised in sheep. Production of DIGIBIND® involves conjugation of digoxin as a hapten to human albumin. Sheep are immunized with this material to produce antibodies specific for the antigenic determinants of the digoxin molecule. The antibody is then papain-digested, and digoxin-specific Fab fragments of the antibody are isolated and purified by affinity chromatography. These antibody fragments have a molecular weight of approximately 46,200 Da. Each vial of DIGIBIND® will bind approximately 0.5 mg of digoxin (or digitoxin), and contains 38 mg of digoxin-specific Fab fragments plus 75 mg of sorbitol as a stabilizer and 28 mg of sodium chloride. The vial contains no preservatives. DIGIBIND® is administered by intravenous injection after reconstitution with Sterile Water for Injection (4 mL per vial), by gentle mixing, to give a clear, colorless, approximately isosmotic solution. Reconstituted product should be used promptly. If it is not used immediately, it may be stored under refrigeration at 2° to 8° C. (36° to 46° F.) for up to 4 hours. The reconstituted product may be diluted with sterile isotonic saline to a convenient volume.

DIGIFAB™ is a sterile, purified, lyophilized preparation of digoxin-immune ovine Fab (monovalent) immunoglobulin fragments. These fragments are obtained from the blood of healthy sheep immunized with a digoxin derivative, digoxin-dicarboxymethoxylamine (DDMA), a digoxin analogue which contains the functionally essential cyclopentaperhydrophenanthrene lactone ring moiety coupled to keyhole limpet hemocyanin. The sheep are pathogen free and are from prion-free herds in Australia. The final product is prepared by isolating the immunoglobulin fraction of the ovine serum, digesting it with papain and isolating the digoxin-specific Fab fragments by affinity chromatography. These antibody fragments have a molecular weight of approximately 46,000 Da. Each vial of DIGIFAB™, will bind approximately 0.5 mg digoxin and contains 40 mg of digoxin immune Fab, approximately 75 mg of mannitol USP, and approximately 2 mg sodium acetate (buffering agent). The product contains no preservatives and is intended for intravenous administration after reconstitution with 4 mL of Sterile Water for Injection USP. The reconstituted product may be added to an appropriate volume of 0.9% sodium chloride for injection.

DIGIBIND® and DIGIFAB™ are not indicated for milder cases of digitalis (digoxin or digitoxin) toxicity and are only indicated for life-threatening or potentially life-threatening digoxin or digitoxin intoxication. Although designed specifically to treat life-threatening digoxin overdose, DIGIBIND® and DIGIFAB™ have also been used successfully to treat life-threatening digitoxin overdose. However, since human experience is limited and the consequences of repeated exposures are unknown, DIGIBIND® and DIGIFAB™ are not indicated for milder cases of digitalis toxicity.

DIGIBIND® and DIGIFAB™ are categorized as "Pregnancy Category C" because it is not known whether these drugs cause fetal harm when administered to a pregnant woman or may affect reproductive capacity. According to the manufacturer's product information, these drugs should be given to a pregnant woman only if clearly indicated for life-threatening digoxin intoxication. Also, it is not known whether digoxin antibodies are excreted in human milk. Because many drugs are excreted in human milk, caution should be exercised when DIGIBIND® or DIGIFAB™ are administered to a nursing woman.

Clinical indications for administration of DIGIBIND® and DIGIFAB™ do not include any condition other than known or suspected life-threatening digoxin or digitoxin intoxication. For purposes of the invention, life-threatening intoxication (sometimes referred to herein simply as "intoxication" or "intoxicated") with exogenous cardenolides and bufadienolides means: (a) fatal doses of 10 mg or more in previously healthy adults or 4 mg in previously healthy children; (b) ingestion causing steady-state serum concentrations greater than 10 ng/mL; or (c) chronic ingestions causing steady-state serum concentrations greater than 6 ng/mL in adults or 4 ng/mL in children. DIGIBIND® and DIGIFAB™ will interfere with digitalis immunoassay measurements. Thus, standard measurement of serum digoxin (or "digoxin") concentration can be clinically misleading until the antibody is eliminated from the body.

For treatment of intoxication, the composition of DIGIBIND® or DIGIFAB™ depends upon the amount of digoxin or digitoxin to be neutralized. However, PIH and MGR are not caused by intoxication from exogenous cardiac glycosides. These conditions are associated with the presence of endogenous factors produced by the mammal that are distinct from known cardiac glycosides, including digoxin, ouabain, bufalin and marinobufagenin. Furthermore, measurements of the concentration of endogenous factors based upon immunoassays for digoxin, ouabain, bufalin or marinobufagenin are known to be inaccurate and likely underestimate the amount of endogenous factors present in the mammal.

As demonstrated by Adair (1996) and Goodlin (1988), antibody compositions effective to treat cardiac glycoside intoxication are not effective to treat preeclampsia. Therefore, effective antibody compositions for treating PIH and IUGR cannot be determined based upon antibody compositions that would be effective to neutralize a similar level of digoxin in a mammal that has ingested an exogenous cardenolide or bufadienolide. Furthermore, therapeutically effective antibody compositions for treating PIH and IUGR cannot be determined solely upon indirect measurements of EFs using immunoassays specific for digoxin, ouabain, bufalin or marinobufagenin.

Compositions of digoxin antibody that are effective for treating digoxin/digitoxin intoxication may be determined by the following formula ("Dtox Formula"):

Dose (units of antibody)=total antigen body load (mgs)÷digoxin binding capacity (mg/unit)

For example, the DIGIBIND® and DIGIFAB™ Dtox Formula used to determine an effective antibody composition for treating intoxication in a patient having a known steady-state serum concentration of digoxin/digitoxin is: number of vials= (D×W)÷100, where "D" is the steady-state serum digoxin concentration and "W" is the patient weight in Kg. Pregnant women with preeclampsia are known to have serum "digoxin" concentrations of approximately ≦1.5, but neither DIGIBIND® nor DIGIFAB™ are approved for treating any condition other than digoxin intoxication. However, even if the EFs in pregnant women were digoxin, neither DIGIBIND® nor DIGIFAB™ would be indicated for treating the low levels observed in pregnant women. Thus, the tables of adult compositions in the DIGIBIND® and DIGIFAB™ product information do not provide any compositions for treating serum digoxin/digitoxin concentrations below 1.0 ng/mL, which would be comparable to the "digoxin" concentrations normally detected in pregnant women with or without preeclampsia.

Table I identifies putative DIGIBIND® of DIGIFAB™ compositions based upon the Dtox Formula for treating serum "digoxin" concentrations in the range that endogenous factors have been measured in pregnant women with and without preeclampsia:

TABLE I

Dtox Formula for DIGIBIND ® or DIGIFAB ™ Dose (mg digoxin binding capacity*)

| Patient Weight | Serum "Digoxin" Concentration (ng/mL) | | | | | | |
|---|---|---|---|---|---|---|---|
| (kg) | 0.1 | 0.2 | 0.4 | 0.8 | 1.2 | 1.6 | 2.0 |
| 40 | 0.02 | 0.04 | 0.08 | 0.16 | 0.24 | 0.32 | 0.4 |
| 60 | 0.03 | 0.06 | 0.12 | 0.24 | 0.36 | 0.48 | 0.6 |
| 70 | 0.035 | 0.07 | 0.14 | 0.28 | 0.42 | 0.56 | 0.7 |
| 80 | 0.04 | 0.08 | 0.16 | 0.32 | 0.48 | 0.64 | 0.8 |
| 100 | 0.05 | 0.10 | 0.20 | 0.40 | 0.60 | 0.80 | 1.0 |
| 120 | 0.06 | 0.12 | 0.24 | 0.48 | 0.72 | 0.96 | 1.2 |
| 140 | 0.07 | 0.14 | 0.28 | 0.56 | 0.84 | 1.12 | 1.4 |

*[weight × digoxin concentration/100] × 0.5 mg digoxin binding capacity per vial Experiments of Goodlin (1988) and Adair (1996) have used the Dtox Formula to determine DIGIBIND® compositions to administer to preeclamptic patients. Goodlin administered a composition of 10 mg DIGIBIND® for a total of 0.13 mgs digoxin binding capacity, resulting in a dose of 0.001 mg digoxin binding capacity per Kg patient body weight (115 Kg patient). Adair administered a composition of 29 mg antibody having a total of 0.38 mg digoxin binding capacity, but the patient weight was not published. Applicant-author's notes indicate the patient weight was 65 Kg. Therefore, Adair administered digoxin binding capacity of 0.0058 mg per Kg patient weight.

Goodlin achieved only a transient, precipitous decrease in mean blood pressure immediately after administration of the antibody, and the results may have been due, in part, to concurrent administration of an antihypertensive drug along with albumin. Adair achieved a gradual reduction in mean arterial pressure, most notably 12 hours after administration of the antibody, but with a concomitant and significant worsening of proteinuria. In both cases the pregnancy was terminated prior to term and the fetuses did not survive. Thus, the Dtox Formula and the antibody compositions administered by Goodlin and Adair have proven to be ineffective in treating preeclampsia. Furthermore, since Adair used a dose of digoxin antibody greater than that used by Goodlin and that higher dose resulted in a significant worsening of proteinuria, it would be expected that even higher doses would have similar or greater adverse side effects. Thus, one would not expect higher doses of digoxin antibody to be therapeutically effective to treat PIH or IUGR.

Surprisingly, Applicant has discovered that symptoms and complications of PIH and IUGR may be effectively treated by administration of a digoxin antibody compositions having as an active ingredient a high dose of digoxin binding capacity, and that such high dose compositions do not cause a worsening of proteinuria. Therapeutically effective high dose digoxin antibody compositions preferably comprise an amount of digoxin antibody sufficient to provide more than 0.006 mgs digoxin binding capacity per Kg patient weight when symptoms or complications of PIH or IUGR are present. Preferably, a high dose composition has digoxin binding capacity that is between ten-fold and one hundred-fold the digoxin binding capacity that would be provided in a composition according to the Dtox Formula. Most preferably, a high dose composition comprises approximately ten-fold the digoxin binding capacity that would be provided in a composition according to the Dtox Formula for treating intoxication evidenced by a similar serum digoxin concentration. Therapeutic compositions less than ten-fold the composition provided according to the Dtox Formula are also effective, provided such compositions have more than 0.006 mg digoxin binding capacity per Kg patient weight if the patient manifests clinical symptoms of PIH or IUGR. Therapeutically effective compositions for prophylaxis may also have less than 0.006 mg digoxin binding capacity per Kg patient weight.

It should be emphasized that the present invention is not limited to digoxin-immune Fab (ovine), DIGIBIND® or DIGIFAB™, or to any particular brand or formulation of digoxin antibody, but encompasses all antibodies, including antigen binding fragments and binding domains, that react immunologically with or bind digoxin. Further the invention is not limited to any particular high dose digoxin antibody composition, dosing method or regimen.

The compositions of the invention comprise a single application dose. A single application dose includes the composition when given (a) entirely in a single administration or (b) when given in aliquots as multiple administrations over a period of time, or (c) when administered continuously over a period of time (e.g., continuous infusion, slow or time release transdermal administration, slow-release or time-release tablets or capsules or caplets). When a composition is given in aliquots over a period of time or is continuously administered over a period of time, preferably the period of time is thirty-six hours or less, more preferably twenty-four hours or less and most preferably twelve hours or less.

The high dose digoxin antibody composition preferably has between approximately 0.5 and 100 mg digoxin binding capacity, more preferably between approximately 1.0 and 50 mg digoxin binding capacity, and most preferably between approximately 1.0 and 15 mg digoxin binding capacity. Sample pharmaceutical compositions of high dose digoxin antibodies appropriate for typical human weights are described in Table II.A and the preferred compositions are provided in Table II.B (approximately 10× DIGIBIND®/DIGIFAB™ Dtox compositions), compositions). Table III represents the preferred compositions of the current formulations of DIGIBIND® or DIGIFAB™ (approximately 10× DIGIBIND®/DIGIFAB™ Dtox compositions), expressed as number of vials. For human or other mammal weights that are greater than 140 Kg, an appropriate composition may be determined by dividing the mammal's weight by 100 and multiplying the result by a digoxin binding capacity within the range of digoxin binding capacities provided in Table II.A. or II.B. for a mammal weighing 100 Kg. For example, if a mammal weighs 500 Kg and has a serum "digoxin" concentration of 1.0 ng/mL, then an appropriate digoxin antibody composition according to Table II.B. is: 500/100×5.0 mg digoxin binding capacity=25 mg digoxin binding capacity (or 50 vials of either DIGIBIND® or DIGIFAB™ in the formulations described in the notes to Table III).

TABLE II.A

Sample Digoxin Antibody Compositions
for PIH and IUGR (mg digoxin binding capacity)

| Patient Weight | Serum "Digoxin" Concentration (ng/mL) | | | | | | |
|---|---|---|---|---|---|---|---|
| (kg) | ≦0.1* | 0.2 | 0.4 | 0.8 | 1.2 | 1.6 | 2.0 |
| 40 | 0.25 | 0.40 | 0.50 | 0.60 | 0.70 | 0.80 | 1.0 |
| 60 | 0.40 | 0.45 | 0.50 | 0.55 | 0.75 | 1.0 | 1.2 |
| 70 | 0.45 | 0.50 | 0.55 | 0.65 | 0.85 | 1.2 | 1.4 |
| 80 | 0.55 | 0.55 | 0.60 | 0.75 | 1.0 | 1.3 | 1.6 |
| 100 | 0.65 | 0.75 | 0.80 | 0.80 | 1.2 | 1.6 | 2.0 |
| 120 | 0.80 | 0.85 | .90. | 1.0 | 1.5 | 2.0 | 2.4 |
| 140 | 0.90 | 1.2 | 1.3 | 1.5 | 1.8 | 2.4 | 2.8 |

*compositions are approximately 0.0065 mg digoxin binding capacity per Kg patient weight.

TABLE II.B

Preferred Digoxin Antibody Compositions**
for PIH and IUGR (mg digoxin binding capacity)

| Patient Weight | Serum "Digoxin" Concentration (ng/mL) | | | | | | |
|---|---|---|---|---|---|---|---|
| (kg) | ≦0.1* | 0.2 | 0.4 | 0.8 | 1.2 | 1.6 | 2.0 |
| 40 | 0.5 | 0.5 | 1.0 | 1.5 | 2.5 | 3.5 | 4.0 |
| 60 | 0.5 | 0.5 | 1.5 | 2.5 | 3.5 | 5.0 | 6.0 |
| 70 | 0.5 | 1.0 | 1.5 | 3.0 | 4.5 | 5.5 | 7.0 |
| 80 | 0.75 | 1.0 | 1.5 | 3.5 | 5.0 | 6.5 | 8.0 |
| 100 | 0.75 | 1.0 | 2.0 | 4.0 | 6.0 | 8.0 | 10.0 |
| 120 | 1.0 | 1.0 | 2.5 | 5.0 | 7.0 | 9.5 | 12.0 |
| 140 | 1.0 | 1.5 | 3.0 | 5.5 | 8.5 | 11.0 | 14.0 |

*compositions suggested for initial prophylactic administration
**most compositions are approximately 10× the dose of DIGIBIND®/DIGIFAB™ as determined by the Dtox Formula

TABLE III

Preferred Digoxin Antibody Compositions of
DIGIBIND®/DIGIFAB™ for PIH and IUGR (in # of vials)

| Patient Weight | Serum "Digoxin" Concentration (ng/mL) | | | | | | |
|---|---|---|---|---|---|---|---|
| (kg) | ≦0.1* | 0.2 | 0.4 | 0.8 | 1.2 | 1.6 | 2.0 |
| 40 | 1 V | 1 V | 2 V | 3 V | 5 V | 7 V | 8 V |
| 60 | 1 V | 1 V | 3 V | 5 V | 7 V | 10 V | 12 V |
| 70 | 1 V | 2 V | 3 V | 6 V | 9 V | 11 V | 14 V |
| 80 | 1.5 V | 2 V | 3 V | 7 V | 10 V | 13 V | 16 V |
| 100 | 1.5 V | 2 V | 4 V | 8 V | 12 V | 16 V | 20 V |
| 120 | 2 V | 3 V | 5 V | 10 V | 15 V | 20 V | 24 V |
| 140 | 2 V | 3 V | 6 V | 12 V | 17 V | 23 V | 28 V |

*compositions appropriate for initial prophylactic administration
V = vials, in most cases constituting approx. 10× Dtox Formula
DIGIBIND: 38 mg antibody/vial, 0.5 mg digoxin binding capacity/vial
DIGIFAB: 40 mg antibody/vial, 0.5 mg digoxin binding capacity/vial In yet another embodiment, the therapeutic composition comprises an amount of digoxin antibody sufficient to provide between greater than 0.006 mg and approximately 10.0 mg digoxin binding capacity per Kg patient body weight, more preferably between approximately greater than 0.006 and approximately 5.0 mgs digoxin binding capacity per Kg patient body weight, even more preferably between approximately 0.01 and 1.0 mg digoxin binding capacity per Kg patient body weight, and most preferably between approximately 0.01 and 0.5 mg digoxin binding capacity per Kg patient body weight.

The compositions of Tables II.A, II.B and III are preferred compositions only, and compositions appropriate for any particular patient weight or serum "digoxin" concentration may have digoxin binding capacity greater than or less than the above amounts, provided that compositions to treat patients manifesting clinical symptoms of PIH or IUGR comprise high dose compositions having greater than 0.006 mg digoxin binding capacity per Kg patient weight (e.g. Table II.A, compositions for serum "digoxin" levels of ≦0.1 ng/mL). For serum "digoxin" concentrations falling between the specific concentrations identified in Tables II.A., II.B and III, in most cases the composition should be given in an amount that is intermediate between the amounts for the next lower and next higher serum "digoxin" concentration for the patient's weight. Similarly, for patient weights falling between those listed in Tables II.A, II.B and III, in most cases the dose should be given for the next highest weight for the particular serum "digoxin" concentration. However, if an intermediate amount may be obtained, the intermediate amount is preferable. For example, if serum "digoxin" concentration is 0.8 ng/mL (whether measured or assumed to be present based upon severity of one or more symptoms) for a patient weight of 115 Kg, a therapeutic composition comprising 9 vials of DIGIBIND® or DIGIFAB™ (Table III) would be administered as a single application dose.

For digoxin antibody formulations (i.e., dosing units), including, without limitation, DIGIBIND® and DIGIFAB™, that have greater or lesser digoxin binding capacity than the DIGIBIND and DIGIFAB formulations of Table III (0.5 mg per vial), antibody compositions should be adjusted to provide digoxin binding capacity that is equivalent to the digoxin binding capacity of the compositions (# vials) described in Table III.

Serum "digoxin" concentration should be obtained before initial administration of digoxin antibody if at all possible. After initial administration, measurements of serum "digoxin" concentration may be misleading because digoxin antibodies are known to interfere with standard digoxin immunoassay and so digoxin antibodies are also expected to interfere with measurement of EFs by digoxin immunoassay. Although it is preferable to measure serum "digoxin" concentration before initial administration of digoxin antibody, it is not necessary to quantify a patient's serum "digoxin" concentration in order to determine a therapeutically effective composition. If serum "digoxin" concentration cannot be readily determined, the subject may be given an initial composition commensurate with the severity of the symptoms of PIH or IUGR. Generally, mild symptoms may initially be treated with a therapeutic composition at the lower end of the therapeutic range for the patient's weight, according to Table II.A, Table II.B., or Table III. Preferably, compositions for mild symptoms and prophylactic treatment are initially selected from the lower range of compositions of Table II.A. The patient should be routinely monitored throughout the course of treatment for improvement, amelioration, stabilization or worsening of symptoms or complications of PIH and IUGR. If the patient response to a composition is adequate in the clinical judgment of the treating physician, then the composition may be repeated as often as needed to maintain the desired response. If an adequate response is not achieved with a composition or a greater response is desired, then a composition having a greater amount of the active ingredient (digoxin binding capacity) should be given in one or more subsequent administrations.

More severe symptoms should be initially treated in the mid-range of the compositions for the patient's weight according to Table II.A, Table II.B or Table III. Again, the patient should be routinely monitored for amelioration, improvement, stabilization or worsening of symptoms or complications of PIH and IUGR, so that the composition may be adjusted (active ingredient decreased or increased) as determined by clinical judgment. For illustration purposes only, and without limitation, a 70 Kg patient presenting with symptoms of severe preeclampsia may be initially administered 3 vials of DIGIBIND® or DIGIFAB™ or digoxin antibody of another formulation having approximately 1.5 mg digoxin binding capacity, but if eclampsia is present the patient may be initially administered a composition of between 4 and 6 vials of DIGIBIND® or DIGIFAB™ or a digoxin antibody composition of another formulation or antibody species having between approximately 2.0 and 3.0 mg digoxin binding capacity.

It is known that pregnant women (normotensive and with PIH) have serum concentrations of endogenous factors in the range of $\leq 0.1$ ng/mL to 1.5 ng/mL (as measured by digoxin immunoassay). It is also known that levels of endogenous factors (as measured by digoxin immunoassay) increase throughout pregnancy (i.e., third trimester>second trimester>first trimester). See, Beyers A D, et al., The possible role of endogenous digitalis—like substance in the causation of pre-eclampsia, *SA Medical Journal* 65:883-885 (1984); Craig H R, et al., Binding of Endogenous Digoxin-like Immunoreactive Factor to Serum Proteins During Normal and Hypertensive Pregnancy, *J. Clin. Immunoassay* 14(4):245-250 (1991); Lopatin D A, et al., *J Hypertension* 17(8): 1179-1187 (1999). Thus, for purposes of the invention a serum "digoxin" concentration may also be selected based upon serum "digoxin" concentrations generally known to be present in pregnant patients, and preferably serum "digoxin" concentrations within the range generally known to be present in patients with PIH. Most preferably, the serum "digoxin" concentration will be based upon the range generally known to be present in PIH, will be selected based upon the state of pregnancy (first, second or third trimester), risk factors for PIH or IUGR (in kind or number), or symptom severity and/or complications commensurate with those of the patient being treated. For example, it is known that patients experiencing symptoms of severe preeclampsia have serum "digoxin" concentrations greater than or equal to 0.3-0.4 ng/mL during the second trimester of pregnancy. Thus, a patient in her second trimester presenting with symptoms of severe preeclampsia may initially be given a composition commensurate with 0.3-0.4 ng/mL, as provided in Tables II.A, II.B or III.

Preferably, the patient is initially given a therapeutic composition having the lowest amount of active ingredient (digoxin binding capacity) appropriate for the patient's weight, as determined by clinical judgment. Thereafter, one or more subsequent compositions having greater amounts of the active ingredient may be administered to achieve the desired improvement in symptoms or complications of PIH or IUGR. However, in situations where the patient's symptoms or complications are potentially life-threatening, it may be preferable to initially administer a therapeutic composition having an amount of the active ingredient greater than the lowest therapeutic composition for the patient's weight.

The digoxin antibody of the composition is any antibody, binding fragment or binding domain that reacts immunologically with or binds digoxin, and preferably an antibody, binding fragment or binding domain specific for a cardenolide or bufadienolide, including, without limitation, anti-ouabain antibody, anti-marinobufagenin antibody, anti-bufalin antibody and anti-digoxin antibody. Methods for quantifying relative cross-reactivity of an antibody for a different antigen or epitope are well known to those skilled in the art. See, for example, Fedorova et al., *Journal of Hypertension* 23(4):835-842 (2005) and references therein. Generally, if an antibody is known to cross-react with digoxin, the cross-reactivity provides a basis to formulate a composition of such antibody to provide the digoxin binding capacity in a therapeutically effective amount as described above. For example, if a formulation of marinobufagenin antibody has 0.5 mg marinobufagenin binding capacity and a cross-reactivity to digoxin of 10%, then the same composition will have approximately 0.05 mg digoxin binding capacity.

The composition may be comprised of whole digoxin antibody, binding fragments, binding domains, or a combination thereof. The digoxin antibody may be polyclonal, monoclonal, chimeric, humanized or fully humanized and may be generated from any known antibody source, including, without limitation, sheep, goat, horse, chicken, rabbit, mouse, mammalian cells lines, bacteria or yeast. The digoxin antibody source is preferably ovine (produced in sheep, or generated or constructed, in whole or in part, from polypeptides, proteins or nucleic acids of ovine origin). Preferably, the digoxin antibody is digoxin immune Fab.

In another embodiment, the composition comprises a therapeutically effective amount that is sufficient to cause a clinically beneficial or a statistically significant reduction in systolic blood pressure, diastolic blood pressure or mean arterial pressure. In alternate embodiments, the composition has a therapeutically effective amount sufficient to cause a clinically beneficial or a statistically significant decrease in proteinuria or a decrease in a patient's serum creatinine level or in a liver enzyme level. Alternatively, the composition has a therapeutically effective amount sufficient to cause a clinically beneficial or a statistically significant increase in urinary output or creatinine clearance.

In another embodiment, the therapeutic composition comprises an amount of digoxin antibody sufficient to cause a reduction in vasospasm, vasoconstriction, exaggerated myocardial function or intravascular volume contraction.

In yet another embodiment, the therapeutic composition comprises an amount of digoxin antibody sufficient to cause an improvement in artery or venous flow, preferably in a middle cerebral artery (fetal or maternal), an umbilical artery or an umbilical vein. Preferably, the amount is sufficient to cause a reduction in or substantial normalization of the S/D ratio or the RI of an artery or vein, or to improve diastolic flow of an artery or vein (e.g., improve the diastolic component of the S/D ratio). Most preferably, the reduction, normalization or improvement is in a middle cerebral artery (fetal or maternal), an umbilical artery or an umbilical vein.

In another embodiment, the composition is therapeutically effective to cause a clinically beneficial or a statistically significant decrease in mean blood pressure (systolic, diastolic or MAP) taken over a period of time. In an alternate embodiment, the therapeutic composition is effective to cause a clinically beneficial or a statistically significant reduction in systolic blood pressure, diastolic blood pressure or mean arterial pressure that commences at a time that is less than four hours after beginning administration of the composition. In an alternate embodiment, the reduction in systolic or diastolic blood pressure or mean arterial pressure commences at a time that is less than four hours after beginning administration of the composition and continues for a period of time that is more than four hours after beginning administration of the composition.

While the above therapeutic compositions have been provided, deviations or modifications may be used, provided that the composition has more than 0.006 mg digoxin binding capacity per Kg patient body weight if the patient manifests clinical symptoms of PIH or IUGR. Furthermore, the compositions simply define a lower limit for treatment of gestational hypertension, preeclampsia, eclampsia and IUGR. Therefore, compositions having higher doses of digoxin binding capacity than the compositions provided in Tables II.A., II.B. and III are also expected to be effective and are also encompassed within the present invention.

A method is also provided for treating gestational hypertension, preeclampsia, eclampsia or IUGR, by administering a therapeutically effective amount of a high dose digoxin antibody composition to a pregnant mammal.

In one embodiment, the method includes the step of administering between greater than 0.006 mg and approximately 10.0 mg of digoxin binding capacity per kilogram of patient body weight. Preferably, the method comprises administration of a digoxin antibody composition having digoxin binding capacity between greater than 0.006 mg and approximately 5.0 mg per kilogram of patient body weight, more preferably between approximately 0.01 mg/Kg and 1.0 mg/Kg patient body weight, and most preferably between approximately 0.01 mg and 0.5 mg/Kg patient body weight.

In yet another embodiment of the invention (FIG. 1), the method includes evaluating a patient for one or more risk factors, diagnostic indicators, causes, symptoms or complications of gestational hypertension, preeclampsia, eclampsia or IUGR. The method may also include determining that the patient does evidence a risk factor, diagnostic indicator, cause, symptom or complication of PIH or IUGR, and then administering a therapeutically effective composition of high dose digoxin antibody commensurate with the clinical assessment.

Administration of the digoxin antibody composition for prophylaxis (e.g., before onset of diagnostic indications or the manifestation of clinical symptoms or complications of PIH or IUGR) is preferably commenced between approximately 14 and 20 weeks' gestation and may be continued throughout the pregnancy for so long as may be medically desirable, advisable or necessary until such time as the patient's symptoms worsen and no longer respond to a therapeutic high dose digoxin antibody composition, or, in the treating physician's clinical judgment, delivery of the fetus is desirable, advisable or necessary. Compositions for prophylaxis may have digoxin binding capacity less than 0.006 mg/Kg patient weight.

In an alternate embodiment, prophylactic administration of a high dose digoxin antibody composition may begin before or after 14 to 20 weeks' gestation, at any time prior to onset of diagnostic indications or the manifestations of clinical symptoms or complications of PIH or IUGR, or at any time after diagnostic tests or patient evaluation indicates the patient is at risk for developing or the likely emergence of gestational hypertension, preeclampsia, eclampsia or intrauterine growth restriction.

Preferably, a therapeutically effective amount of a high dose digoxin antibody composition is given for prophylaxis when the patient has one or more risk factors for PIH or IUGR, including those risk factors from among the group risk factors consisting of first pregnancies, pregnant women under the age of 20 or over the age of 35, women of black race, women who conceive through IVF, women who have a prior pregnancy with a different partner or have a long interval between pregnancies, multi-gestational pregnancies, women with a personal or family history of PIH or IUGR, women who are of higher than normal weight or body mass index (>25) prior to pregnancy, women who have thrombophilia risk factors, and women with a personal or familial history of polycystic ovarian syndrome, diabetes, hypertension, renal (kidney) disease, rheumatoid arthritis, systemic lupus erythematosus, other autoimmune disease or multiple sclerosis.

In yet another embodiment of the method, administration of the high dose digoxin antibody composition is given intravenously, as a continuous infusion or in the form of a bolus infusion or a bolus injection. A continuous infusion is preferably given over a period of 36 hours or less, more preferably over 24 hours or less, and most preferably over twelve hours or less. A bolus infusion is preferably given by administration of the dose by infusion over a period longer than 10 minutes and less than or equal to 1 hour, preferably over thirty minutes. A bolus injection is preferably given by administration of the dosage over a period of ten minutes or less. Alternatively, the digoxin antibody may be administered via intramuscular or subcutaneous or transdermal injection or infusion.

In yet another embodiment of the method, administration of a high dose digoxin antibody composition is repeated. The same high dose digoxin antibody composition may be repeated. Alternatively, the repeated administration is of a high dose digoxin antibody composition that is greater than or less than a previously administered composition. The composition to be given in any repeat administration is determined by clinical judgment based upon patient symptoms, responsiveness to one or more prior high dose digoxin antibody compositions (e.g., the medical parameters described above that determine therapeutic effectiveness) or based upon other appropriate medical criteria.

In an alternate embodiment, a repeat administration of a high dose digoxin antibody composition is given between approximately one and thirty-six hours after a prior administration of a high dose digoxin antibody, preferably between approximately one and twenty-four hours, more preferably between one and fifteen hours, even more preferably between three to eight hours, and most preferably at approximately six hours.

In a preferred embodiment, the high dose digoxin antibody composition is repeatedly administered on a fixed schedule, the fixed schedule being between approximately every one and every thirty-six hours, more preferably between approximately every one and every twenty-four hours, even more preferably between every one and fifteen hours, yet even more preferably between every three and every eight hours, and most preferably approximately every six hours.

Therapeutically effective high dose digoxin antibody compositions may be sufficient to reduce blood pressure to such an extent that antihypertensive agents are not required. However, a high dose digoxin antibody composition may also be administered with antihypertensive agents. In one embodiment, the method comprises administration of a high dose digoxin antibody and a therapeutically effective amount of an antihypertensive agent. The antihypertensive agent may be administered prior to, subsequent to, or concurrent with the administration of the high dose digoxin antibody composition. Preferably the antihypertensive agent is selected from among the group consisting of hydralazine, nifedipine, sodium nitroprusside, 1-methyldopa (e.g., Aldomet®), atenolol and labetalol. Dosing amounts and regimens for administering these antihypertensive agents during pregnancy are well known in the art. Generally, a therapeutically effective amount of hydralazine is between 10 mg and 100 mg, preferably hydralazine is administered orally as 10 mg, 25 mg, 50 mg or 100 mg tablets. Alternatively, hydralazine may be administered intravenously. Preferably, hydralazine is administered at least once per 24 hours. Generally, a therapeutically effective amount of nifedipine is between 10 mg and 100 mg. Preferably, a dose of nifedipine is administered orally at least once per 24 hours. Generally, a therapeutically effective amount of methyldopa (e.g., Aldomet) is between 250 and 3000 mg. Methyldopa may be administered orally, preferably as 15 mg, 25 mg, 30 mg, 50 mg, 125 mg, 250 mg or 500 mg tablets. Alternatively, methyldopa may be administered intravenously. Generally, a therapeutically effective amount of atenolol is between 5 mg and 100 mg, preferably between 25 and 100 mg. Preferably, a dose of atenolol is administered orally at least once per 24 hours. Generally, an effective amount of sodium nitroprusside is administered intravenously between 0.1 µg/Kg/minute and 0.6 µg/Kg/minute.

Preferably, the antihypertensive is labetalol. The patient is preferably administered 20 mg labetalol by intravenous injection over two minutes. In an alternate embodiment, the patient is repeatedly administered labetalol by injection, preferably in doses between approximately 20 mg and 80 mg, and most preferably approximately every ten to fifteen minutes. Alternatively, labetalol may be administered as a continuous infusion. Preferably 20 to 80 mg labetalol is infused at a rate of 1.0 mg/minute. The labetalol dose may be adjusted as indicated by patient response and clinical judgment. Preferably, labetalol is given in a maximum aggregate dose of 240 mg.

In yet another embodiment, the method further comprises administration of a therapeutically effective amount of a pharmaceutical agent to improve fetal development or to limit the adverse effects of premature delivery on the neonate. Preferably the pharmaceutical agent is a corticosteroid to enhance fetal lung maturity, to reduce the incidence or severity of respiratory disease in the neonate or to lessen periventricular or intraventricular hemorrhage or neurological damage in the neonate. Most preferably the corticosteroid is bethamethasone or dexamethasone.

In yet another embodiment, the corticosteroid is administered at least twice during a consecutive period of forty-eight hours. Corticosteroids are even more preferably given by intramuscular injection of 12 mgs bethamethasone every twenty-four hours or intramuscular injection of 6 mgs dexamethasone every twelve hours, during a period of at least forty-eight consecutive hours.

Corticosteroids are preferably administered either at least 30 minutes prior to or at least 30 minutes after the administration of a digoxin antibody composition. In yet another embodiment, the corticosteroid is administered at least 12 hours prior to administration of a first dose of digoxin antibody. In another embodiment, the second dose of corticosteroid is administered at least 6 hours prior to a subsequent dose of digoxin antibody.

In another embodiment the method further comprises administration of an effective amount of an anti-convulsant, preferably magnesium sulfate or phenytoin. Generally, a therapeutically effective amount of phenytoin is between 10 and 100 mg. Preferably, phenytoin is administered at least once per 24 hours, and may be administered two or three times per 24 hours.

In yet another embodiment, an effective amount of magnesium sulfate may be administered prior to, subsequent to, or concurrent with administration of the digoxin antibody composition. Preferably, magnesium sulfate (100 mL of a 0.5 gm/mL solution, or 50 gm) is added to 400 mL normal saline for a total volume of 500 mL. Administration is preferably by intravenous infusion over 30 minutes. Administration of magnesium sulfate may be repeated periodically or administered continuously. The patient is preferably administered a loading dose of magnesium sulfate intravenously, most preferably the loading dose is 6 gm or 60 mL of a 0.1 gm/mL solution. Preferably, after administration of a loading dose of magnesium sulfate the dosing is maintained at 2 gm/hr (20 mL/hr).

In yet another embodiment, the antibody composition is administered in combination with intravenous fluids, preferably lactated Ringer's solution. Most preferably, intravenous fluids are combined with magnesium sulfate for administration at a total fluid rate between 40 mL/hr and 250 mL/hr, preferably 125 mL/hour. Intravenous fluids may be adjusted during the course of digoxin antibody treatment as determined by clinical judgment.

In an alternate embodiment of the method, one or more repeat doses of a high dose digoxin antibody composition are independently selected (i.e., a prior composition is not automatically repeated) prior to administration, allowing the treatment to be adjusted over time based upon the individual patient condition, response to prior digoxin antibody compositions (e.g., the medical parameters that determine effectiveness, as described above) and other relevant medical or dosing criteria.

In yet another embodiment of the method, during a consecutive period of thirty hours of less, the subject is administered one or more high dose digoxin antibody compositions having an aggregate digoxin binding capacity of at least 0.032 mg per kilogram of patient weight. Alternatively, during a period of thirty hours or less the patient is administered one or more high dose digoxin antibody composition having an aggregate digoxin binding capacity between approximately 0.032 mg and less than or approximately equal to 0.171 mg per kilogram of the patient's weight. In another embodiment, the aggregate digoxin binding capacity administered in one or more high dose digoxin antibody compositions over a consecutive 30 hour period or less is between approximately 0.066 mg and approximately 0.171 mg per kilogram of the patient's weight. In yet another embodiment, the aggregate digoxin binding capacity administered in one or more compositions over a 30 hour period or less is between approximately 0.081 mg and approximately 0.171 mg per kilogram of the patient's body weight. In yet another embodiment, the aggregate digoxin binding capacity administered in one or more compositions over a 30 hour period or less is between approximately 0.122 mg and approximately 0.171 mg per kilogram of the patient's weight.

Another embodiment of the invention provides a method for treating gestational hypertension, preeclampsia, eclampsia or intrauterine growth restriction, comprising the step of administering at least one composition of a digoxin antibody from among the range of compositions described in Table II.A., Table II.B or Table III, so as to provide a composition having greater than 0.006 digoxin binding capacity per kilogram of the patient's weight. In yet another embodiment, the composition is selected from any one of Tables II.A, II.B or Table III based upon the patient's weight.

In yet another embodiment of the method, the high dose digoxin antibody composition is given to a patient to treat intrauterine growth restriction. The umbilical artery flow velocity in a preeclamptic patient is illustrated in FIG. 3. Preeclamptic vasoconstriction reduces the blood flow velocity through arteries and veins, particularly the middle cerebral artery (maternal or fetal), an umbilical artery or the umbilical vein. Reduced flow, particularly in the umbilical artery results in the flow velocity "bottoming out" during diastole (indicated in FIG. 3 as "C" and in FIG. 4a) such that little or no blood is flowing to the fetus and/or placenta. This results in a high systolic/end diastolic ("S/D") ratio and a high resistance index ("RI"). Reduction in artery flow or venous flow, particularly in the middle cerebral artery or an umbilical artery or the umbilical vein, restricts oxygenation, fluid exchange and nutrition, potentially causing growth restriction of the fetus. Administration of a high dose digoxin antibody composition eases vasoconstriction in arteries and veins, and as shown in FIG. 4b, and results in a decrease in or substantial normalization of the S/D ratio and/or RI of a middle cerebral artery (maternal or fetal), an umbilical artery or the umbilical vein.

In one embodiment, the method includes administration of a high dose digoxin antibody composition to substantially normalize the S/D ratio of the middle cerebral artery (maternal or fetal), or to improve the S/D ratio of an umbilical artery or the umbilical vein. In yet another embodiment, the high dose digoxin antibody composition is administered to substantially normalize the RI of the middle cerebral artery (maternal or fetal), or to improve the RI of an umbilical artery or umbilical vein.

While the above compositions have been provided, deviations or modifications may be used. Again, the therapeutically effective high dose compositions described above simply define a lower limit of compositions providing greater than 0.006 mg digoxin binding capacity per kilogram patient weight when a patient manifests clinical symptoms of PIH or IUGR; therefore, effective compositions having digoxin binding capacity higher than this lower limit, or greater than any of the examples specifically provided herein, are also expected to be effective and so all such compositions are also encompassed within the present invention. Similarly, high dose compositions for prophylaxis may comprise digoxin binding capacity that is less than 0.006 mg per Kg patient weight, and although not specifically provided in the Tables and examples provided herein, all such compositions are encompassed within the present invention.

VIII. Biological and Prophetic Examples

The method is further illustrated in the following non-limiting examples.

Biological Example #1

A 16-year-old 70 Kg primigravida at 29 weeks 5/7 days presented with a presumed diagnosis of eclampsia. Her prenatal course had been uncomplicated until the day of admission. Her past medical history was negative for chronic illness. The patient had complaints of scotomata, persistent headache, and reported seizure activity for two episodes prior to hospital arrival and one on the labor deck. Initial evaluation revealed an alert patient with obvious postictal behavior. Her blood pressure was elevated to approximately 160/110s and otherwise had stable vital signs. Physical examination revealed arterio-venous nicking on opthoscalmic exam, 4+ edema of the lower extremities and obvious facial and upper extremity edema. Deep tendon reflexes were 3+ with 2 beats of clonus. The remainder of the complete exam was within normal limits. Lab evaluation of the urine noted proteinuria on qualitative analysis of 2+ and a urine specific gravity of 1.020. Serum chemistry revealed hyperuricacidemia at 8.1, elevated serum creatinine of 1.0, BUN of 6, and otherwise normal electrolytes and liver enzymes. The complete blood count revealed a platelet count of 429,000, white count of 10.4 and a hemoglobin and hematocrit of 12.0 and 35.6, respectively. The ammonia level was 3 and coagulation studies were normal. Urine drug screening was negative for substances of abuse including cocaine and methamphetamines. CT scanning of the maternal head failed to reveal any pathological abnormalities.

Ultrasound examination revealed a single gestation with a breech presentation. The estimated gestational age was consistent with the previously determined age of 29 weeks with an estimated fetal weight of 1331 grams. The amniotic fluid index was 5.42 cm and fetal breathing, movement, and tone were noted to be present. Doppler flow studies of the umbilical artery revealed an elevated S/D ratio of 5.6, RI of 0.82, and minimal diastolic flow. No anatomical abnormalities were noted on exam. Fetal cardiotocograph revealed a baseline of 135 with minimal beat-to-beat variability. Occasional non-repetitive decelerations were noted with good recovery. They were deemed to be non-ominous.

The patient was placed on intravenous magnesium sulfate. Central venous access and arterial line placement were performed. After informed discussion with the immediate family including the option to stabilize with compassionate off label use of fragmented antibody to digoxin and to administer corticosteroids for fetal benefit, the patient's mother provided consent.

Standard preeclampsia monitoring every hour was followed with one on one nursing in the intensive care unit. Based upon a level of 0.4 ng/mL serum "digoxin" concentration (believed to be present but not quantified), digoxin immune Fab (0.5 mg digoxin bound per vial) was administered (time=$T_0$) in a composition of 3 vials digoxin immune Fab for a total digoxin binding capacity of 1.5 mg. The composition was administered via an intravenous bolus infusion over thirty (30) minutes. Intravenously administered fluids were standardized to 125 cc/hr.

Urine output from admission to time of digoxin immune Fab (ovine) infusion (5 hours) was 300 cc (60 cc/hr). Over the first 6 hours post initial administration of digoxin immune Fab, the average urinary output increased to 70 cc/hr with blood pressure readings of 148 to 162 systolic and 104 to 111 diastolic. Due to insufficient response and continuing elevated blood pressure, at 6 hours after the initial dosage ($T_6$), a second dose was administered based upon a serum digoxin concentration of 0.8 ng/mL (concentration believed to be present due to severity of symptoms, but not quantified), resulting in a composition of 6 vials for a total of 3.0 mg digoxin binding capacity. After administration of the second dose, urine output increased to an average of 140 cc/hr. The next dose ($T_{12}$) was omitted due to sustained clinical improvement. Doses were administered at approximately $T_{18}$ and $T_{24}$, each totaling 3.0 mg digoxin binding capacity. Doses were administered at approximately $T_{30}$ and $T_{36}$, but due to clinical improvement the doses were each decreased to 1.5 mg digoxin binding capacity. The final dose was given approximately 12 hours prior to the time of anticipated delivery. During the period of digoxin antibody dosing, a diuresis of 7426 cc occurred for an average output of 177 cc/hr. The total intake of intravenous fluids during the same time period was 5923 cc. The urine qualitative exam at $T_{10}$ revealed negative proteinuria with a specific gravity of 1.011. Urine osmolality at $T_{40}$ was 125 (normal 500 to 800 mosm). The serum creatinine level decreased to 0.7 with the remainder of electrolytes remaining normal. Serial blood pressure measurements during the period from the doubling of the dose until deliver ranged from 130s-140s systolic, 80s-90s diastolic. From the time of admission until 12 hours following delivery, no antihypertensives were required. The edema resolved in the face and upper extremities, with significant decreases in the lower extremity edema to 1+. Deep tendon reflexes improved to 1+ with no clonus.

Fetal assessment during this time showed no changes in the cardiotocograph. Ultrasound examination every 6 hours revealed a reassuring biophysical profile score of 8 of 10. Doppler flow assessment of the umbilical artery every 6 hours revealed a decreasing systolic/diastolic ratio with an increasing diastolic component. The S/D ratio at $T_{15}$ was 3.2 with a RI of 0.69, suggesting that fetal hemodynamics were improved.

Cesarean delivery was performed at 48 hours post-administration of corticosteroids secondary to a breech presentation. The delivery was attended by NICU and resulted in a live birth of a female child. Apgar scores were 7 and 8 at one and five minutes, respectively. The neonate did not require any oxygen support and was admitted to the neonatal intensive care unit secondary to prematurity size of 1290 grams. The neonate did not require oxygen during hospitalization and had no sepsis or intraventricular hemorrhage. She was discharged home on the 31st day of life.

The maternal postoperative course was complicated by elevated blood pressures of 140s-160s systolic and diastolic readings in the 100s. The patient was started on metoprolol 100 mg twice daily. She was discharged home on postoperative day #4 with stable blood pressures controlled with metoprolol. All follow up laboratory tests remained within normal limits. The neonate had no adverse sequelae and was discharged home on day of life #31. A medical history was obtained from the mother 22 months following delivery. The mother reported no chronic health problems, was not on any medications and had no hospitalizations since delivery. The child was evaluated by a pediatrician at 19 months of age. The pediatrician reported the child to be well, of normal growth and normal development.

Biological Example #2

A 19 year old 74 Kg gravida 1, para 0 female at 29 weeks gestational age was transferred to the tertiary care center due to elevated blood pressure, dizziness, and excessive body edema most pronounced on face, hands, feet (2+). The patient was experiencing headache, blurred vision, epigastric pain, and shortness of breath. Blood pressure was reported as 140-160s 80-90s, with a recording of 143/90 and a pulse of 61 at admission. A grade 2⅗ murmur with click was noted by the maternal fetal medicine (MFM) specialist. Past medical history was positive for spina bifida with no neurologic impairment. The family history was positive for birth defects (heart disease and deafness), Grave's disease, and hypertension. The patient had experienced no problems during pregnancy prior to the day of admission. The patient was admitted for surveillance and work-up of preeclampsia and steroid administration. She was given oxygen and intravenous fluids.

Ultrasound evaluation of fetus revealed fetal heart tones (FHTs) in the 150s with acceleration. Fetal size was consistent with given dates. Doppler blood flow studies preinfusion revealed an S/D ratio of 4.84 and an RI of 0.79. Corticosteroid (betamethasone) was administered to accelerate fetal lung maturity. A cardiology consult was obtained due to maternal bradycardia (HR 50-66) and heart murmur. EKG showed sinus bradycardia and shortened PR interval. Echocardiography revealed left ventricular hypertrophy with minimal pericardial effusion and sinus bradycardia with no ectopy. Cardiology cleared the patient for surgery.

In the first 24 hours following admission the patient experienced oliguria. The initial 24 hour urine resulted in 400 ml total volume and revealed 16.5 gm of protein. Due to the oliguria, a composition of 6 vials (3 mgs digoxin binding capacity) of digoxin immune Fab were administered as an intravenous bolus over thirty (30) minutes, based upon a serum "digoxin" level of 8.0 ng/mL (believed to be present but not quantified). A second dose of 6 vials was administered approximately 15 hours after the initial dose. Urinary output (UOP) was noted to improve with an increase to 800 ml for the next 24 hour urine with in protein to 11.8 gm. Doppler blood flow (umbilical artery) improved with a decrease in the S/D ratio to 2.87.

A cesarean section and appendectomy were performed approximately 48 hours post initial administration of steroids. The surgery was tolerated well, and the post-operative course was uneventful with the exception of leukocytosis, which was possibly attributed to the steroid administration.

The patient delivered a viable female infant, 1476 gm with Apgar scores of 7 and 9. The baby was transferred to the NICU in stable condition. She did not experience Respiratory Distress Syndrome, sepsis, or intraventricular hemorrhage. Her respiratory diagnosis was Transient Tachypnea of the Neonate and she required CPAP×2 days and oxygen for a total of 3 days. She was discharged home on day 28 of life.

The mother received prophylactic magnesium sulfate for 24 hours post delivery. She was discharged on postpartum day 4 on vitamins and pain medication. The mother and child were evaluated 18 months after delivery. The mother indicated she had no health problems, no hospitalizations since delivery and in not on medication other than birth control. The infant was examined by a pediatrician who reported the infant to be physically and developmentally normal and thriving.

Biological Example #3

A 20 year old 91 Kg gravida 1, para 0 female presented to her local obstetrician at 31 weeks with a 5 lb weight gain, blood pressure 222/112, and 3+ proteinuria. Prenatal care to this point was uncomplicated although she did have trichomonas early in the pregnancy. The family history is pertinent in that the patient's mother had chronic hypertension and had preeclampsia with all three of her pregnancies. The patient was hospitalized for stabilization and delivery. A maternal fetal medicine consult was obtained at which time the patient reported scotomata and headache. There was no bleeding, leakage, contractions, right upper quadrant pain, or pre-ictal symptoms. There was 1+ pitting edema in the lower extremities with some edema in the lower sacral area. Clinical lab was unremarkable with the exception of 3+ proteinuria and a slightly elevated LDH. Good fetal movement was noted. On ultrasound, the fetus was vertex, anterior grade II placenta. Fetal size was consistent with the stated age of 31 weeks with an estimated weight of 1499-1570 grams. Doppler exam showed absent diastolic flow in the umbilical artery with compensatory changes in the middle cerebral arteries. Resistance index was 0.78 with an S/D ratio of 4.7. Amniotic fluid index was about 4 cm. The biophysical profile was 6 out of 10 with no decelerations, decreased variability, no contractions, and good movement and tone. The diagnoses were severe preeclampsia, abnormal Doppler flow with absent diastolic flow, oligohydramnios, and hypertensive urgency.

Upon admission magnesium sulfate was initiated. Within three hours of admission the patient was also on labetalol via continuous IV and had received hydralazine 5 mg IV×2. Blood pressure was in the 140-160/100 range following antihypertensive treatment. Corticosteroid (betamethasone) was administered to enhance pulmonary maturation of the fetus.

Because of insufficient antihypertensive response and diminished/absent fetal blood flow, digoxin immune Fab was administered. An initial dose (time=$T_0$) was determined using a serum "digoxin" concentration of 0.9 ng/mL (believed to be present but not quantified), resulting in a composition of 8 vials (0.5 mg digoxin bound per vial) totaling 4 mg digoxin binding capacity. The composition was administered by intravenous bolus infusion over thirty (30) minutes. A second dosage (approximately $T_{28}$) and third dosage (approximately $T_{43}$), each of 4 vials (2 mg total digoxin binding capacity per dose), were administered based upon a serum "digoxin" concentration of 4.5 ng/mL (believed to be present, but not quantified). The patient's symptoms improved overnight with BPs 130s-150s/70s-90s. Urinary output increased and edema decreased. Creatinine clearance (CrCl), measured on two occasions, increased from 147 on the second hospital day to 169 on the third hospital day. Fetal testing was reassuring. On repeat Doppler, diastolic flow was noted.

At approximately 48 hours post initial administration of steroid a 1520 gram viable male infant was delivered via cesarean section. Apgar scores were 6 and 9. The infant's respiratory diagnosis was Prolonged Transition and he initially required no respiratory support. On day 4 the infant developed clinical sepsis and necrotizing enterocolitis (NEC) and required surgery to repair an ileal perforation. He was on the ventilator for 3 days post op, then weaned to room air for the remainder of his hospitalization. He experienced a Grade I intraventricular hemorrhage. He was discharged home at 64 days of age.

Following delivery the patient's blood pressure remained elevated 140s-150s systolic, 80s-100s diastolic with labetalol. Nifedipine was initiated in attempt to wean the patient from labetalol. Otherwise, the patient was progressing well. She was discharged home on post op day 4. At 18 months post delivery, a medical history was obtained from the mother and the child was examined by a neonatologist and children's physical therapist. The mother reported no chronic health complications and no hospitalizations since delivery; she was not on any medications. The neonatologist found no abnormalities with the exception of rhinorrhea and an abdominal scar. He described the child as healthy and thriving. The physical therapist found the developmental exam to be normal with motor level and other levels somewhat advanced for adjusted age. The child no longer requires follow-up with pediatric surgeon for ileal perforation and has no dietary limitations.

Biological Example #4

A 29 year old 123 Kg gravida 3, para 2 female was air evacuated from a remote non-tertiary hospital to a tertiary care center after experiencing two seizures and amaurosis fugax (complete blindness). The first seizure occurred at home and the second was witnessed by paramedics. Pregnancy history was notable for preeclampsia in the immediate preceding pregnancy. This pregnancy was complicated by cholelithiasis and elevated BP for one week. Past medical and surgical histories were non-contributory. Family history was pertinent in that her mother has epilepsy. The patient was transported on magnesium sulfate.

On admission to the tertiary center the patient's treatment continued with intravenous magnesium sulfate and administration of betamethasone to improve neonatal respiratory outcomes. She was alert and oriented ×3 and was experiencing headache, blurred vision and diplopia. Blood pressure was in the 150s/90s. Urine protein was reported as 3+ at the referring hospital. Physical exam was notable for swelling in the hands and face as well as 3+ pitting edema in the extremities with 4+ deep tendon reflexes and 1 beat of clonus. Admission 24-hour urine revealed a creatinine clearance of 98.2 with 1590 mg of protein. The patient's condition was considered critical. She required oxygen administration and placement of a central venous line. A one-time dose of labetalol 20 mg was administered IV push in response to a BP of 162/109.

Primarily because of low urinary output, digoxin immune Fab was initiated, based upon a serum "digoxin" level of 4.0 ng/mL (believed to be present, but not quantified), a composition of 5 vials (0.5 mg digoxin binding capacity per vial) was administered by bolus infusion over thirty (30) minutes. The 5 vial dosage was repeated every six hours for 8 additional doses. A total antibody composition comprising approximately 22.5 mgs digoxin binding capacity was administered over the course of treatment. During the hospital course the patient's clinical condition improved. Clinical lab results improved and BP was relatively stable. Doppler flow studies showed improvement. Although no pre-infusion values are available, the S/D ratio improved from 4.1 to 2.9, respectively, at 48 hours and 108 hours post initial antibody injection. It was decided to delay delivery.

The magnesium sulfate and digoxin immune Fab were discontinued following the eighth dose and the patient remained stable for approximately 24 hours after which there was an increase in blood pressure. A ninth dose of 5 vials of digoxin immune Fab was administered with a marginal decrease in BP and an increase in urinary output.

Five days following admission the patient delivered via cesarean section a 30 3/7 GA, 1181 gram male infant with Apgar scores of 8 and 9. The infant was transported on room air to the NICU due to prematurity. Despite his prematurity and small size, the infant did not experience Respiratory Distress Syndrome and did not require ventilatory support. His respiratory diagnosis was pulmonary insufficiency of prematurity and he required nasal CPAP for 2 days and oxygen-therapy for a total of 11 days. A patent ductus arteriosus was successfully closed with indomethacin. The infant experienced no sepsis or intracranial hemorrhage. He was discharged home on an apnea monitor at 36 days of age.

The maternal postpartum course was uneventful. Blood pressure remained elevated and the patient was treated with oral antihypertensives. The mother was discharged on the 8$^{th}$ hospital day with routine medications as well as labetalol 100 mg bid orally. Both the mother and child received follow-up evaluations 2 months post delivery. The mother reported no current medical problems and no hospitalizations since delivery. She was not on any medications. The 2 month old infant was examined by a neonatologist and children's physical therapist. The physical exam was normal. The infant had emesis and apnea associated with feeds and this was attributed due to overfeeding. The neonatologist recommended a volume decrease. The physical therapy exam was normal.

Biological Example #5

A 17 year old 62 Kg gravida 1, para 0 female at 34½ weeks (33 weeks by ultrasound) was found unresponsive, presumably postictal, and was brought to the local emergency room. She subsequently was witnessed undergoing generalized tonic-clonic seizures. Blood pressures were significantly elevated (160s/100s). Laboratory values on presentation included a uric acid of 13, dipstick urine protein of 3+ and serum creatinine of 1.4. The patient was combative and unresponsive to commands. There were multiple small lacerations, abrasions, and contusions to the face and extremities. Past medical history was negative. The patient was treated with midazolam, hydralazine and labetalol.

The patient was then transported to a tertiary care setting. On arrival the patient continued to exhibit combativeness and altered mental status. Blood pressure was 151/107. Deep tendon reflexes were absent. Vaginal bleeding was noted along with uterine tetany suggestive of abruption. Uterine activity was noted to be consistent with a hyperstimulatory pattern. The fetus was exhibiting severe variable decelerations with decreased variability. The patient was taken to the operating room where she had a cesarean section under general anesthesia. There was 30% abruption of the placenta. A 2104 gram male infant was delivered with Apgar scores of 6, 8, and 9. The infant was taken to intensive care in stable condition.

The patient was treated postoperatively with intravenous magnesium sulfate. During the postpartum period she remained combative with altered mental status for 3 days. A neurologic consult was obtained. The patient was bent in the fetal position, and was arousable to touch but would moan and flail extremities. She was uncommunicative and unable to follow commands. A CT scan of the brain revealed findings consistent with hypertensive encephalopathy related to eclampsia. Hydralazine was given for BP and phenergan and meperidine for pain. A propofol drip, midazolam drip and lorazepam were administered for agitation/sedation. The midazolam drip and restraints were employed throughout most of the period of postpartum encephalopathy. Blood pressure remained elevated, 140-150s/90s. Follow-up neurologic assessments revealed little change.

Due to continued symptoms of hypertensive encephalopathy, digoxin immune Fab was administered based upon a level of 0.6 ng/mL serum "digoxin" concentration, resulting in a composition of 4 vials for a total of 2.0 mgs digoxin binding capacity. The composition was administered by intravenous bolus infusion over thirty (30) minutes. Within 5 minutes of infusing digoxin immune Fab the patient became responsive to commands and verbally communicative, with marked improvement. She was alert and responsive, and was asking appropriately for her infant and for something to eat. The physician noted that the eclampsia post-ictal resolved 5 minutes after administration of antibody. Sedatives were weaned. On the day following antibody administration the patient was transferred out of ICU. On the sixth postpartum day the patient was discharged on labetalol for hypertension, and ibuprofen and oxycodone/acetaminophen for pain.

Biological Example #6

Endogenous digoxin-like factors have been reported by some investigators to be elevated in preeclampsia. If present, then the site of action for these inhibitors could be Na$^+$/K$^+$ ATPase. To test this possibility, erythrocyte Na$^+$/K$^+$ ATPase activity was determined in pregnancies complicated by severe preeclampsia, in normotensive pregnancies and in healthy non-pregnant women. Whole blood was obtained from 12 subjects in each of the three categories. Erythrocytes were isolated and placed in cocktails of HEPES buffer solution at a 50% hematocrit and incubated with $^{86}$Rubidium (Rb$^+$), a potassium analog, for three hours. Na$^+$/K$^+$ ATPase activity was determined by the uptake of the Rb$^+$, in erythrocytes and expressed as nmol/hr/10$^6$ cells. Erythrocyte Na$^+$/K$^+$ ATPase activity was significantly increased in normotensive pregnancies as compared to normotensive non-pregnant subjects (81.4±8.2 nmol/hour/10$^6$ cells, vs 61.1±7.4 nmol/hour/10$^6$ cells, mean±S.D., p<0.01). Erythrocyte Na$^+$/K$^+$ ATPase activity was significantly decreased in severe preeclamptic patients as compared to normotensive pregnancies (46.4±14.1 nmol/hour/10$^6$ cells).

The effect of digoxin antibody on erythrocyte Na$^+$/K$^+$ ATPase activity in severe preeclampsia was also evaluated. Whole blood was obtained from 12 normotensive pregnant women and 12 severe preeclamptic women. Erythrocytes were isolated and placed in cocktails of HEPES buffer solution at a 50% hematocrit and incubated with Rb$^+$. Digoxin antibody in the form of DIGIBIND® was administered to 6 preeclamptic patients and normal saline placebo was administered to 6 preeclamptic patients at the time of umbilical cord clamping. DIGIBIND® was administered in a 50 cc normal saline bag using a dose calculated by the formula of an endogenous digitalis like factor of 0.2 ng/mL and compositions appropriate for each patient's weight were selected from Table III.

Na$^+$/K$^+$ ATPase activity was determined at baseline (delivery), 6, 12 and 24 hours by the uptake of Rb$^+$ in erythrocytes and expressed as nmol/hr/10$^6$ cells. Mean Na$^+$/K$^+$ ATPase activity increased toward normal controls in both the DIGIBIND® and placebo treated preeclamptic samples; however, for the placebo treated preeclamptic samples, the increase in activity appeared to be more gradual and modest. (See Table IV below).

TABLE IV

Digoxin Antibody Effect on Sodium/Potassium ATPase Activity*

| Group | Baseline | 6 hours | 12 hours | 24 hours |
|---|---|---|---|---|
| Normal Control Samples (N = 12) | 82.2 ± 8.2 | 79.0 ± 11.9 | 82.6 ± 8.4 | 86.1 ± 14.3 |
| Digibind ® Treated Samples (N = 6) | 48.4 ± 18.4 | 63.2 ± 19.3 | 62.0 ± 9.1 | 73.8 ± 24.3 |
| Placebo Treated Samples (N = 6) | 44.0 ± 9.3 | 51.8 ± 14.5 | 53.8 ± 12.0 | 59.5 ± 12.4 |

*Activity expressed as $^{86}Rb^+$ uptake nmol/hr/$10^6$ RBC

Biological Example #7

Digoxin antibody (specifically DIGIBIND® or DIGIFAB™, referred to as "DFAB") will be evaluated in a clinical trial. This study will be a double-blind, placebo-controlled, randomized trial of the efficacy of digoxin antibody for the treatment of 26 patients with severe preeclampsia. Patients must meet both diagnostic criteria for preeclampsia and meet at least criteria for severe preeclampsia, as defined by the American College of Obstetrics and Gynecology. No participant will have received digoxin. After obtaining informed consent, patients will be randomized 1:1 to receive either digoxin antibody or placebo (normal saline) over 48 hours (8 total single application doses). A total of 13 patients will receive DFAB and 13 patients will receive placebo (normal saline). The DFAB doses (mg digoxin binding capacity) will be determined using a serum "digoxin" concentration of 0.6 ng/mL and compositions appropriate for each patient's weight will be selected from Table III. Compositions will be administered approximately every six hours. The contents of individual vials should be first dissolved with 4 ml of sterile water for injection, by gentle mixing, to give a clear, colorless solution. The reconstituted vials should be collectively diluted in normal saline to a total of 50 cc. The study drug should be administered as an intravenous bolus injection over a 10 minute period. Patients will be assessed at screen (baseline) and monitored over the 48 hour period of study drug administration.

Blood pressure measurements will be obtained hourly. A significant difference in mean arterial pressure is expected within four hours after administration of each application dose with significant lowering in the DFAB group from baseline, and the trend is expected to continue through at least 6 hours. Patients will be allowed antihypertensive therapy if the clinician determines such therapy is necessary. It is expected that there will be a statistically significant difference between the groups with 46% of the patients in the placebo group expected to require antihypertensives and none of the patients in the DFAB group are expected to require antihypertensives (p<0.01).

Creatinine clearance will be calculated by the standard formula: Clearance (ml/min)=$U_{Cr} \times V/P_{Cr}$ where $U_{Cr}$=urine creatinine concentration in mg/dL; V=urine volume in mL/min.; and $P_{Cr}$=plasma creatinine in mg/dL. A statistically significant increase in 24 hour creatinine clearance from baseline is also expected for the DFAB group (DFAB 147±23 mL/min.; placebo 95±25 ml/min., p≦0.05). However, a 30% increase in creatinine clearance from baseline (representing approximately 30 mL/min.) in the DFAB group versus the placebo group would be considered a clinically beneficial change.

A clinically beneficial or statistically significant decrease in proteinuria is expected during study drug administration. If baseline is between >1+ and <3+ on urine dipstick (i.e., >300 mg but <500 mg/24 hr), it will be considered clinically beneficial for a decrease from baseline to negative proteinuria. A statistically significant decrease is expected for baseline proteinuria≧3+ (≧500 mg/24 hr) if reduction from baseline is ≧33% (p≦0.05). No adverse events are expected in any patient.

Biological Example #8

A 19 year old, 70 kg nulliparous, gravida 2, with a familial history of preeclampsia would present to the obstetrician at 28 weeks' gestation for routine prenatal exam. Prior blood pressures would be in the range of 90-110 systolic, 70s diastolic. At 28 weeks, blood pressure would be 130/90 and urine dipstick of <1. Physical exam suggested fetal growth restriction so Doppler blood flow studies would be indicated. Doppler would reveal an S/D ratio of 4.0 and an RI of 0.78, and intrauterine growth restriction (fetal size consistent with 25 week gestation). Serum "digoxin" concentration would be undetectable. Due to increasing blood pressures, reduced umbilical artery flow, and intrauterine growth restriction in a multifetal gestation and with a history of preeclampsia (patient's mother and sister), the patient would be indicated for treatment with digoxin immune Fab. The patient would initially be indicated for an intramuscular injection of 40 mgs digoxin immune Fab (DIGIFAB™) having a total of 0.5 mgs digoxin binding capacity. The patient would initially be administered 40 mg (0.5 mg digoxin binding capacity) digoxin immune Fab (DIGIFAB™) by intramuscular injection at least once each week and instructed to self-monitor and report daily blood pressure measurements. Frequency and/or doses of digoxin immune Fab treatment would be increased if blood pressure measurements increase. Patient would be evaluated for blood pressure and proteinuria on weekly follow-up visits. On follow-up visits from 29 weeks to 35 weeks, blood pressure would be in 120s-130s systolic, 70s-80s diastolic, doppler blood flow of umbilical artery would show improvement with a S/D ratio of 2.5 and reassuring biophysical profile, dipstick<1 and normal urinary output and normal serum creatinine levels.

If at 36 weeks, the patient's weight is 82 Kg, with a BP 140/90, proteinuria is observed 1+, and/or umbilical doppler indicates an increase in umbilical artery constriction (e.g., S/D of 4.5) or absent diastolic flow, then the patient would be admitted to the hospital with an anticipated delivery in approximately 48 hours. Bethamethasone (12 mgs intramuscular) would be administered upon hospital admission and approximately 12 hours later. Approximately 60 minutes after bethamethasone injection, the patient would be given a loading dose of 4 vials (160 mgs, total 2 mgs digoxin binding capacity) digoxin immune Fab (DIGIFAB™) by bolus infusion. Total intravenous fluids would be standardized to 125 cc/hr and digoxin immune Fab would be continued as an infusion at a rate of 4 mg per hour. During DIGIFAB™ administration, mean BPs are expected to be in the 120s-130s systolic, 70s-80s diastolic and protein dipstick is expected to be <1. Umbilical artery flow is expected to show improvement (e.g., S/D of 2.5) with an increased diastolic component.

A second dose of 12 mgs bethamethasone would be administered approximately 24 hours after admission, and delivery would be performed approximately 24 hours after the last dose of bethamethasone. Two viable neonates would be delivered having Apgars of 7 and 8.

In addition to object, features and advantages in the embodiments and examples described above, other objects, features and advantages of the present invention will be apparent to those skilled in the art. From time to time various professional medical organizations may modify the medical criteria for diagnosis of preeclampsia and eclampsia, and the present invention is not limited to the specific clinical symptoms, indications or diagnostic factors described herein.

While preferred examples and steps of the present invention have been illustrated and described, this has been by way of illustration and the invention should not be limited except as required by the scope of the appended claims and their equivalents.

TABLE V

Summary Biological Examples Nos. 1-5*

| # | Indication for Treatment | Preeclampsia Eclampsia or IUGR | Patient Weight | Dose Regimen | Response | Effective |
|---|---|---|---|---|---|---|
| 1 | Hypertension; ↓ urine output; ↓ fetal blood flow | Eclampsia/ at risk for IUGR | 70 Kg | $T_0$ - 3 vials $T_{12, 18, 24}$ - 6 vials $T_{30, 36}$ - 3 vials Dose in first 30 hrs: 0.171 mg/kg | ↓BP ↑ urinary output ↓ proteinuria ↓ edema ↑ fetal blood flow ↓ serum creatinine ↓ deep tendon reflexes | Yes |
| 2 | Oliguria; ↓ fetal blood flow | Severe preeclampsia/ at risk for IUGR | 74 Kg | $T_0$ - 6 vials $T_{15}$ - 6 vials Dose in first 30 hrs: 0.081 mg/kg | ↑ urinary output ↑ fetal blood flow | Yes |
| 3 | Hypertension; ↓ (or absent) fetal blood flow | Severe preeclampsia/at risk for IUGR | 91 Kg | $T_0$ - 8 vials $T_{28}$ - 4 vials $T_{43}$ - 4 vials Dose in first 30 hrs: 0.066 mg/kg | ↓ BP ↓ edema ↑ fetal blood flow ↑ creatinine clearance | Yes |
| 4 | ↓urinary output; ↓ fetal blood flow | Eclampsia/ At risk for IUGR | 123 Kg | $T_{0, 6, 12, 18, 24, 30, 36, 42}$ - 5 vials $T_{66}$ - 5 vials Dose in first 30 hrs: 0.122 mg/kg | ↓BP ↑urinary output ↑fetal blood flow | Yes |
| 5 | Hypertensive; Eclamptic Encephalopathy | eclampsia with encephalopathy | 62 Kg | 4 vials 0.032 mg/kg | restoration of mental status | Yes |

*Biological Examples #1-5 represent individual case reports. Results of cellular assays (#6), prophetic clinical trials (#7) and prophetic individual case examples are not included in this Table V.

What is claimed is:

1. A method of extending pregnancy in a gravid human patient by reducing endogenous inhibition of Na+, K+ ATPase activity in a cell of the gravid human patient exhibiting at least one symptom of gestational hypertension, preeclampsia, eclampsia, or intrauterine growth restriction comprising administration of a dosage of digoxin antibody to the gravid human patient, wherein the dosage is effective to reduce endogenous inhibition of Na+, K+ ATPase activity and extend pregnancy in the patient.

2. The method of claim 1, wherein the patient exhibits proteinuria levels greater than 300 mg over an interval of 24 hours prior to administration.

3. The method of claim 2, comprising administration of subsequent doses of digoxin antibody at least until the levels of proteinuria in the gravid human patient decrease after administration.

4. The method of claim 1, wherein the at least one symptom includes hypertension greater than 140 mm Hg systolic or 90 mm Hg diastolic and proteinuria greater than 300 mg per 24 hours.

5. The method of claim 1, wherein the at least one symptom includes hypertension greater than 160 mm Hg systolic or 110 mm Hg diastolic and proteinuria greater than 500 mg per 24 hours.

6. The method of claim 1, wherein the at least one symptom includes hypertension greater than 140 mm Hg systolic or 90 mm Hg diastolic and proteinuria greater than 1+ on two random urine dipstick samples collected at least 4 hours apart.

7. The method of claim 1, wherein the at least one symptom includes hypertension greater than 160 mm Hg systolic or 110 mm Hg diastolic and proteinuria greater than 3+ on two random urine dipstick samples collected at least 4 hours apart.

8. The method of claim 1, wherein the dosage is administered over a period of six hours or less.

9. The method of claim 8 comprising administration of subsequent dosages of digoxin immune Fab.

10. The method of claim 1, wherein the method further comprises administering a therapeutically effective amount of corticosteroid.

11. The method of claim 1, wherein the method further comprises administering a therapeutically effective amount of an antihypertensive drug.

12. The method of claim 11, wherein the antihypertensive drug is labetalol, altenolol, nifedipine, 1-methyldopa or hydralazine.

13. The method of claim 1, wherein the method further comprises administering a therapeutically effective amount of magnesium sulfate or phenytoin.

14. The method of claim 1, wherein the digoxin immune Fab is ovine digoxin immune Fab.

15. A method of extending pregnancy in a gravid human patient by increasing Na+, K+ ATPase activity in a cell of the gravid human patient exhibiting endogenous inhibition of Na+, K+ ATPase, comprising administration of a dosage of digoxin antibody to the gravid human patient, wherein the dosage is effective to increase Na+, K+ ATPase activity and extend pregnancy in the human patient.

16. The method of claim 15, wherein the patient exhibits proteinuria levels greater than 300 mg over an interval of 24 hours prior to administration.

17. The method of claim 16, comprising administration of subsequent doses of digoxin antibody at least until the levels of proteinuria in the gravid human patient decrease after administration.

18. The method of claim 15, wherein the at least one symptom includes hypertension greater than 140 mm Hg systolic or 90 mm Hg diastolic and proteinuria greater than 300 mg per 24 hours.

19. The method of claim 15, wherein the at least one symptom includes hypertension greater than 160 mm Hg systolic or 110 mm Hg diastolic and proteinuria greater than 500 mg per 24 hours.

20. The method of claim 15, wherein the at least one symptom includes hypertension greater than 140 mm Hg systolic or 90 mm Hg diastolic and proteinuria greater than 1+ on two random urine dipstick samples collected at least 4 hours apart.

21. The method of claim 15, wherein the at least one symptom includes hypertension greater than 160 mm Hg systolic or 110 mm Hg diastolic and proteinuria greater than 3+ on two random urine dipstick samples collected at least 4 hours apart.

22. The method of claim 15, wherein the dosage is administered over a period of six hours or less.

23. The method of claim 22, comprising administration of subsequent dosages of digoxin immune Fab.

24. The method of claim 15, wherein the method further comprises administering a therapeutically effective amount of corticosteroid.

25. The method of claim 15, wherein the method further comprises administering a therapeutically effective amount of an antihypertensive drug.

26. The method of claim 25, wherein the antihypertensive drug is labetalol, altenolol, nifedipine, 1-methyldopa or hydralazine.

27. The method of claim 15, wherein the method further comprises administering a therapeutically effective amount of magnesium sulfate or phenytoin.

28. The method of claim 15, wherein the digoxin immune Fab is ovine digoxin immune Fab.

\* \* \* \* \*